United States Patent [19]

Luly et al.

[11] Patent Number: 5,604,294

[45] Date of Patent: Feb. 18, 1997

[54] MACROCYCLIC IMMUNOMODULATORS

[76] Inventors: Jay R. Luly, 1021 Mayfair; Megumi Kawai, 746 Kenwood Dr.; Yat S. Or, 1107 Washington Ave.; Paul E. Wiedeman, 144 W. Park Ave.; Rolf Wagner, 6293 Old Farm La., all of Libertyville, Ill. 60048

[21] Appl. No.: 213,318

[22] Filed: Mar. 14, 1994

Related U.S. Application Data

[63] Continuation-in-part of Ser. No. 149,416, Nov. 9, 1993, abandoned, which is a continuation-in-part of Ser. No. 32,958, Mar. 17, 1993, abandoned, which is a continuation-in-part of PCT/92/07600, Sep. 8, 1992 published as WO93/04680, Mar. 18, 1993, which is a continuation-in-part of Ser. No. 755,208, Sep. 5, 1991, abandoned.

[51] Int. Cl.$^6$ .................. C07D 491/16; A61K 31/395
[52] U.S. Cl. ........................................... 540/456
[58] Field of Search ..................... 540/456; 514/291, 514/411, 183

[56] References Cited

U.S. PATENT DOCUMENTS

| 5,149,701 | 3/1993 | Shaflee et al. | 540/456 |
| 5,284,840 | 2/1994 | Rupprecht et al. | 540/456 |
| 5,284,877 | 2/1994 | Organ et al. | 540/456 |

FOREIGN PATENT DOCUMENTS

| WO93/04680 | 3/1993 | WIPO | 540/456 |

*Primary Examiner*—Robert T. Bond

[57] ABSTRACT

Immunomodulatory macrocyclic compounds having the formula

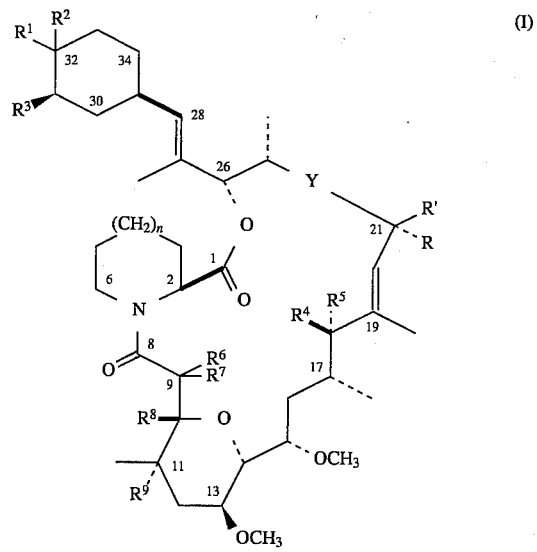

and the pharmaceutically acceptable salts, esters, amides and prodrugs thereof, wherein Y is selected from one of the formulae

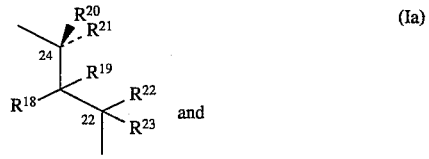

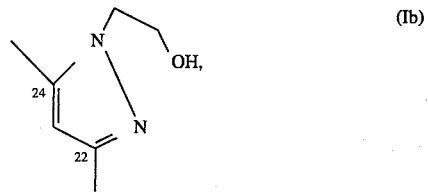

as well as pharmaceutical compositions containing the same and methods of their use.

11 Claims, No Drawings

MACROCYCLIC IMMUNOMODULATORS

This application is a continuation-in-part of U.S. patent application Ser. No. 08/149,416, filed Nov. 9, 1993, abandoned, which is a continuation-in-part of U.S. patent application Ser. No. 08/032,958, filed Mar. 17, 1993, abandoned, which is a continuation-in-part of International Patent Application No. PCT/US92/07600, filed Sep. 8, 1992, which is a continuation-in-part of U.S. patent application Ser. No. 07/755,208, filed Sep. 5, 1991 and now abandoned.

FIELD OF THE INVENTION

The present invention relates to novel chemical compounds having immunomodulatory activity, and in particular to macrolide immunosuppressants. More particularly, the invention relates to semisynthetic analogues of ascomycin and FK-506, means for their preparation, pharmaceutical compositions containing such compounds and methods of treatment employing the same.

BACKGROUND OF THE INVENTION

The compound cyclosporine (cyclosporin A) has found wide use since its introduction in the fields of organ transplantation and immunomodulation, and has brought about a significant increase in the success rate for transplantation procedures. Unsatisfactory side-effects associated with cyclosporine, however, such as nephrotoxicity, have led to a continued search for immunosuppresant compounds having improved efficacy and safety.

Recently, several classes of macrocyclic compounds having potent immunomodulatory activity have been discovered. Okuhara et al., in European Patent Application No. 184162, published Jun. 11, 1986, disclose a number of macrocyclic compounds isolated from the genus Streptomyces. Immunosuppresent FK-506, isolated from a strain of $S.$ $tsukubaensis$, is a 23-membered macrocyclic lactone represented by formula 1a, below. Other related natural products, such as FR-9000520 (1b) and FR-900523 (1c), which differ from FK-506 in their alkyl substituent at C-21, have been isolated from $S.$ $hygroscopicus$ $yakushimnaensis$. Yet another analog, FR-900525, produced by $S.$ $tsukubaensis$, differs from FK-506 in the replacement of a pipecolic acid moiety with a proline group.

FR-900520, also known as ascomycin, has been previously disclosed by Arai et al. in U.S. Pat. No. 3,244,592, issued Apr. 5, 1966, where the compound is described as an antifungal agent. Monoghan, R. L., et al., on the other hand, describe the use of ascomycin as an immunosuppressant in European Patent Application No. 323865, published Jul. 12, 1989.

Although the immunosuppressive activity of FK-506 has been clinically confirmed, toxicity in mammals has limited its utility. The activity of FK-506 has, however, prompted efforts to discover novel analogs of FK-type compounds which possess superior properties. These efforts include the isolation of new fermentation products, the microbial transformation of existing chemical entities, the chemical modification of these macrocycles, and the synthesis of hybrid species derived from smaller synthetic fragments.

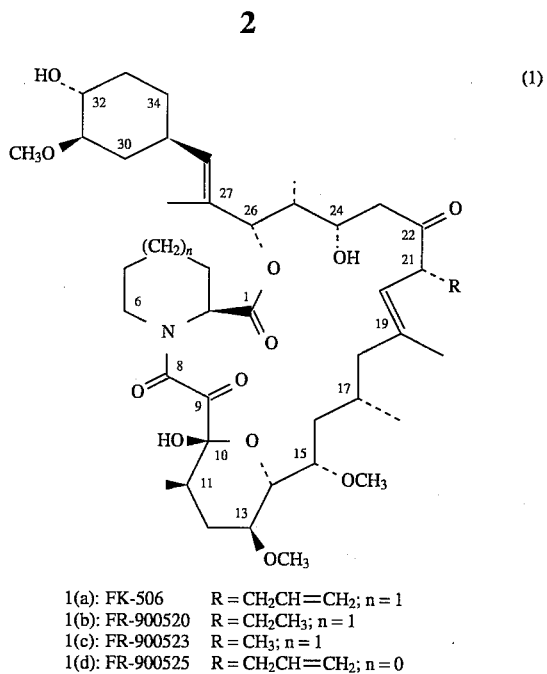

1(a): FK-506    R = CH$_2$CH=CH$_2$; n = 1
1(b): FR-900520    R = CH$_2$CH$_3$; n = 1
1(c): FR-900523    R = CH$_3$; n = 1
1(d): FR-900525    R = CH$_2$CH=CH$_2$; n = 0

Fermentation products of FK-type compounds include C-21-epi derivatives of FK-506; a 31-demethylated derivative of FK-506; 31-oxo-FK-506; and compounds derived from FK-506, FR-900523 and FR-900525 which are characterized by the introduction of hydroxy-protecting groups, formation of a double bond by elimination of water between carbons 23 and 24, oxidation of the hydroxy group at carbon 24 to the ketone, and reduction of the allyl side-chain at carbon 21 via hydrogenation. Other published derivatives include those derived from FK-506 and FR-900520 where the lactone ring is contracted to give a macrocyclic ring containing two fewer carbons.

Several microbial transformations of FK-type compounds at carbon 13 have been published, such as the microbial demethylation of FR-900520 to form the bis-demethylated 13,31-dihydroxy ring-rearranged derivation of FR-900520; the microbial monodemethylation of FK-506 and FR-900520, respectively; and the microbial demethylation of FR-900520 at C-31, as well as a number of other macrocyclic microbial transformation products.

Numerous chemical modifications of the the FK-type compounds have been attempted. These include the preparation of small synthetic fragments of FK-type derivatives; a thermal rearrangement of a variety of derivatives of FK-506 which expands the macrocyclic ring by two carbons; and modifications which include methyl ether formation at C-32 and/or C-24, oxidation of C-32 alcohol to the ketone, and epoxide formation at C-9.

Although some of these modified compounds exhibit immunosuppressive activity, the need remains for macrocyclic immunosuppressives which do not have the serious side effects frequently associated with immunosuppressive therapy. Accordingly, one object of the invention is to provide novel semisynthetic macrolides which possess the desired immunomodulatory activity but which may be found to minimize untoward side effects.

Another object of the present invention is to provide synthetic processes for the preparation of such compounds from starting materials obtained by fermentation, as well as chemical intermediates useful in such synthetic processes.

A further object of the invention is to provide pharmaceutical compositions containing, as an active ingredient,

3 one of the above compounds. Yet another object of the invention is to provide a method of treating a variety of disease states, including post-transplant tissue rejection and autoimmune disfunction.

SUMMARY OF THE INVENTION

In one aspect of the present invention are disclosed compounds having the formula

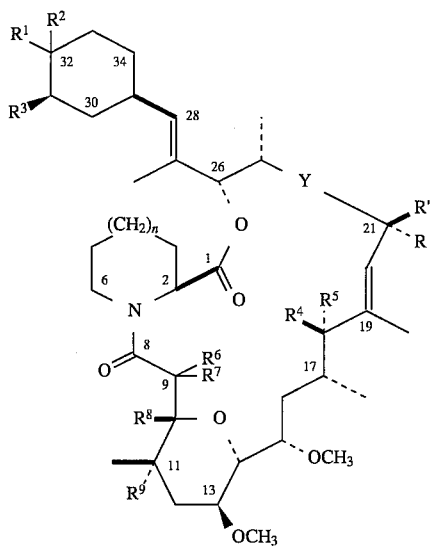
(I)

wherein n, R, R', $R^1$, $R^2$, $R^3$, $R^4$, $R^5$, $R^6$, $R^7$, $R^8$, and $R^9$ are defined below.

When examined for immunomodulatory activity using a common in vitro biological assay, the compounds of the invention are seen to be potent immunosuppressants. Consequently, it is expected that the compounds may be found to possess immunosuppressive, antimicrobial, antifungal, antiviral, antiinflammatory, and antiproliferative activity, as well as the ability to reverse chemotherapeutic drug resistance.

Accordingly, in another aspect of the present invention are disclosed pharmaceutical compositions comprising a compound of the invention in combination with a pharmaceutically acceptable carrier. Suitable carriers and methods of formulation are also disclosed.

In a further aspect of the present invention are disclosed processes for the preparation of the above compounds, synthetic intermediates useful in the preparations of these and other immunomodulator derivatives of ascomycin, and methods of immunomodulatory treatment by the administration of a therapeutically effective amount of a compound of the invention to a patient in need of such treatment.

DETAILED DESCRIPTION OF THE INVENTION

The compounds of the present invention, which may be formed by modification of FR-900520 (ascomycin) or one of its congeners (such as FK-506, etc.), are those described by the general formula:

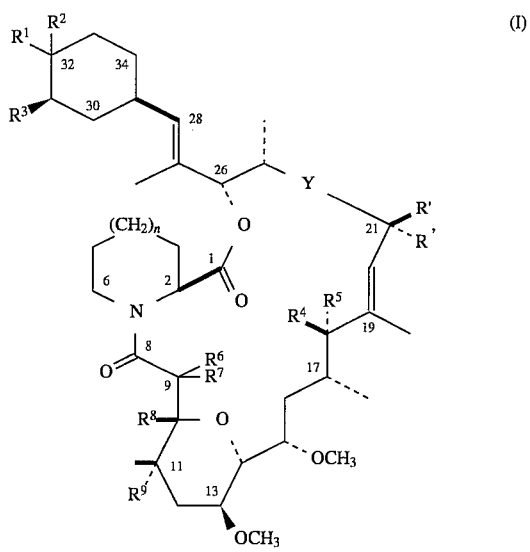
(I)

wherein n is zero or one;
R and R' are chosen such that one of R and R' is hydrogen, and the other is methyl, ethyl, 2-hydroxyethyl, propyl, cyclopropylmethyl, 2-oxopropyl, 2-ethanal or allyl;
$R^1$ is hydrogen, and $R^2$ and $R^3$ are independently selected from:
  (a) —OC(S)$OR^{10}$, provided that one of $R^{20}$ and $R^{21}$ is simultaneously —OC(S)$OR^{12}$;
  (b) —OC(O)$R^{14}$; provided that one of $R^{20}$ and $R^{21}$ is simultaneously —OC(O)$R^{15}$,
  (c) —C(=NH)$CCl_3$;
  (d) —OC(O)$CH_2$I:
  (e) —OP(O)$(OR^{10})_2$; and
  (f) loweralkoxy, provided that $R^2$ and $R^3$ may not both be loweralkoxy; alternatively, $R^1$ and $R^2$ taken together are =NNHC(O)$NH_2$;
$R^4$ and $R^5$ are selected from:
  (a) hydrogen;
  (b) —$OR^{11}$;
  (c) halogen; and
  (d) hydroxy, provided that when one of $R^4$ and $R^5$ is hydroxy, the other is hydrogen; alternatively, $R^4$ and $R^5$ taken together form a divalent radical selected from the group consisting of oxo and thiooxo;
Y is a selected from:

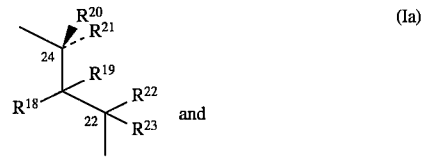
(Ia)

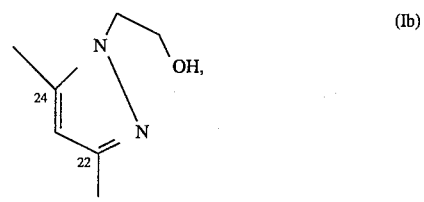
(Ib)

where $R^{18}$ and $R^{19}$ are chosen such that:
  (i) both of $R^{18}$ and $R^{19}$ are hydrogen, or
  (ii) one of $R^{18}$ and $R^{19}$, taken together with one of $R^{20}$ and $R^{21}$, forms a C-23/C-24 bond, and the other of $R^{18}$ and $R^{19}$ is hydrogen;
$R^{20}$ and $R^{21}$ are chosen such that:

(i) one of $R^{20}$ and $R^{21}$ is hydrogen, and the other of $R^{20}$ and $R^{21}$ is:
  (a) hydrogen,
  (b) hydroxy,
  (c) amino,
  (d) —N(CH$_2$CH$_2$)$_2$N—R$^{12}$,
  (e) —N(CH$_2$CH$_2$)$_2$NH,
  (f) —OR$^{12}$,
  (g) —OC(O)NHR$^{24}$, where $R^{24}$ is:
    (1) hydrogen,
    (2) loweralkyl, or
    (3) aryl,
  (h) —C(O)R$^{12}$,
  (i) —OC(S)OR$^{12}$,
  (j) —OC(O)R$^{15}$,
  (k) —OC(O)CH$_2$I, or
  (l) —O—(hydroxyl protecting group); or
(ii) one of $R^{20}$ and $R^{21}$, taken together with one of $R^{18}$ and $R^{19}$, forms a C-23/C-24 bond, and the other is:
  (a) hydrogen,
  (b) hydroxy, or
  (c) loweralkoxy;
alternatively, $R^{20}$ and $R^{21}$ taken together from an oxo group; $R^{22}$ and $R^{23}$ are chosen such that:
  (i) both are loweralkoxy; or
  (ii) one of $R^{22}$ and $R^{23}$ is hydrogen, and the other is:
    (a) hydroxy,
    (b) —OC(O)R$^{13}$, or
    (c) —OC(O)O—(arylalkyl-);
alternatively, $R^{22}$ and $R^{23}$ taken together form an oxo group; $R^6$ and $R^7$ are chosen such that:
  (i) both of $R^6$ and $R^7$ are hydrogen:
  (ii) one of $R^6$ and $R^7$ is hydrogen, and the other of $R^6$ and $R^7$, taken together with $R^8$, forms a C-9/C-10 bond;
  (iii) one of $R^6$ and $R^7$ is hydroxy, and the other of $R^6$ and $R^7$ is:
    (a) hydrogen,
    (b) loweralkyl,
    (c) arylalkyl, or
    (d) aryl;
or, taken together, $R^6$ and $R^7$ form a divalent radical selected from:
  (a) oxo,
  (b) =NOH,
  (c) =NNHC(O)NH$_2$,
  (d) =NNR$^{25}$R$^{26}$, where $R^{25}$ and $R^{26}$ are independently:
    (1) hydrogen,
    (2) loweralkyl, or
    (3) aryl,
  (e) =CH$_2$,
  (f) —O—CH$_2$—, and
  (g) thiooxo:
alternatively, $R^6$ and $R^7$, taken together with the carbon to which they are attached, are absent such that C-8 is attached directly to C-10;
$R^8$ is selected from:
  (a) hydroxy,
  (b) halogen,
  (c) amino,
  (d) loweralkylamino,
  (e) arylalkylamino,
  (f) loweralkoxy, and
  (g) arylalkoxy;
alternatively, $R^8$, taken together with one of $R^6$ and $R^7$, forms a C-9/C-10 double bond or, taken together with $R^9$, forms a C-10/C-11 double bond; and
$R^9$ is hydrogen or, taken together with $R^8$, forms a C-10/C11 bond.
In the above, $R^{10}$, $R^{11}$, $R^{12}$ and $R^{13}$ are each independently loweralkyl, arylalkyl or aryl; and
$R^{14}$ and $R^{15}$ are each independently:
  (i) 2-nitro-aryl,
  (ii) 3-nitro-aryl,
  (iii) 4-nitro-aryl,
  (iv) 2-pyridyl,
  (v) 3-pyridyl, or
  (vi) 4-pyridyl.

Preferred among the compounds of the present invention are those in which R and R' are methyl, ethyl, propyl or allyl; $R^4$ and $R^5$ are both hydrogen; one of $R^4$ and $R^5$ is hydroxy, and the other of $R^4$ and $R^5$ is hydrogen; $R^{20}$ is hydroxy; $R^{20}$ and $R^{21}$ are both hydrogen; $R^{22}$ and $R^{23}$, taken together, form an oxo group; $R^6$ and $R^7$, taken together, form an oxo group; $R^8$ is hydroxy; and/or $R^9$ is hydrogen.

Representative of particularly preferred compounds of the present invention are those demonstrated in Examples 9 and 19, below.

When examined for immunomodulatory activity using a common in vitro biological assay, the compounds of the invention are seen to be potent immunomodulatory agents. Consequently, it is expected that the compounds will possess immunomodulatory, antimicrobial, antifungal, antiviral, antiinflammatory and antiproliferative activity. Moreover, the compounds of the invention would be expected to possess the ability to reverse chemotherapeutic drug resistance. As agents with block T-cell activation, a prerequisite for HIV proliferation, the compounds may be useful as prophylactics for the prevention of HIV replication. While, the compounds of the invention would be useful when used independently of other agents, combination therapy with other immunosuppressants would be expected to be beneficial as well. These other agents include but are not limited to FK-506, rapamycin, cyclosporin A, mycophenolic acid, azathioprine, prednisolone, cyclophosphamide, brequinar and leflunomide.

As used throughout this specification and in the appended claims, the following terms have the meanings specified:

The term "acyl" as used herein refers to an aryl or alkyl group, as defined below, appended to a carbonyl group including, but not limited to, acetyl, pivaloyl, benzoyl and the like. The term "alkenyl" as used herein refers to straight or branched chain groups of 2 to 12 carbon atoms containing one or more carbon—carbon double bonds including, but not limited to ethenyl, 1-propenyl, 2-propenyl, 2-methyl-1-propenyl, 1-propenyl, 1-butenyl, 2-butenyl and the like.

The terms "alkoxy", "alkylether" and "loweralkoxy" as used herein refer to a loweralkyl group, as defined below, attached to the remainder f the molecule through an oxygen atom including, but not limited to, methoxy, ethoxy, isopropoxy, n-butoxy, sec-butoxy, isobutoxy, tert-butoxy and the like.

The term "alkoxycarbonyl" as used herein refers to an alkoxy group, as defined above, attached via a carbonyl group including, but not limited to, methyloxycarbonyl, ethyloxycarbonyl, tert-butyloxycarbonyl, cyclohexyloxycarbonyl and the like.

The term "alkyl" as used herein refers to a monovalent straight chain or branched chain group of 1 to 12 carbon atoms including, but not limited to, methyl, ethyl, n-propyl, isopropyl, n-butyl, sec-butyl, isobutyl, tert-butyl and the like.

The terms "alkylamino" and "loweralkylamino" as used herein refers to a group having the structure —NH—(loweralkyl), where the loweralkyl portion is as defined below. Alkylamino and loweralkylamino groups include, for example, methylamino, ethylamino, isopropylamino and the like.

The term "aryl" as used herein refers to carbocyclic aromatic groups including, but not limited to, phenyl, 1- or 2-naphthyl, fluorenyl, (1,2)-dihydronaphthyl, (1,2,3,4)-tetrahydronaphthyl, indenyl, indanyl and the like, substituted by $R^{111}$, $R^{112}$ and $R^{113}$; where the substituents $R^{111}$, $R^{112}$ and $R^{113}$ are either independently selected from the group consisting of:

(a) hydrogen, (b) —($C_1$-to-$C_7$ alkyl), where alkyl is as defined above, (c) —($C_2$-to-$C_6$ alkenyl), where alkenyl is as defined above, (d) halogen, where halogen is as defined below, (e) —$(CH_2)_m N(C_1$-to-$C_3$ alkyl$)_2$, where m is zero to six, (f) —CN (g) —CHO (h) mono-, di-, tri-, or perhalogenated alkyl, (i) —$S(O)_s(C_1$-to-$C_3$ alkyl), where s is zero, one or two, (j) —$C(O)N(C_1$-to-$C_3$ alkyl$)_2$, (k) —$(CH_2)_m O(C_1$-to-$C_3$ alkyl), where m is as defined above, (l) —$CH(OR^{115})(OR^{116})$, where $R^{115}$ and $R^{116}$ are independently —($C_1$-to-$C_3$ alkyl) or, taken together, form an ethylene or propylene bridge, (m) —$(CH_2)_m OC(O)(C_1$-to-$C_3$ alkyl), where m is as defined above, (n) —$(CH_2)_m C(O)O(C_1$-to-$C_3$ alkyl), where m is as defined above, (o) —$OR^{117}$, where $R^{117}$ is selected from:

(i) —$PO(OH)O^- M^+$, wherein $M^{30}$ is a proton or a positively charged inorganic or organic counterion, (ii) —$SO_3^- M^+$, where $M^+$ is as defined above, and (iii) —$C(O)(CH_2)_m C(O)O^- M^+$, where m and $M^+$ are as defined above, (p) —$S(O)_t N(C_1$-to-$C_3$ alkyl$)_2$, where t is one or two, (q) —$NO_2$, (r) —$N_3$, and (s) guanidino, where guanidino is as defined below, or taken together, any two of adjacent $R^{111}$, $R^{112}$ and $R^{113}$ form a carbocyclic ring having 5, 6, or 7 ring atoms.

The terms "arylalkoxy" and "arylalkylether" as used herein refer to an arylalky group, as defined below, attached to the parent molecular moiety through an oxygen atom. Arylalkoxy includes, but is not limited to, benzyloxy, 2-phenethyloxy, 1-naphthylmethyloxy and the like.

The term "arylalkyl" as used herein refers to an aryl group, as previously defined, appended to an alkyl group including, but not limited to, benzyl, 1- and 2-naphthylmethyl, halobenzyl, alkoxybenzyl, hydroxybenzyl, aminobenzyl, nitrobenzyl, guanidinobenzyl, fluorenylmethyl, phenylmethyl(benzyl), 1-phenylethyl, 2-phenylethyl, 1-naphthylethyl and the like.

The term "arylalkylamino" as used herein refers to a group having the structure —NH—(arylalkyl), where the arylalkyl portion is as previously defined. Examples of arylalkylamino groups include benzylamino, 1-phenylethylamino and the like.

The terms "aryloxy" and "arylether" as used herein refer to an aryl group, as defined above, attached to the parent molecular moiety through an oxygen atom. Aryloxy includes, but is not limited to, phenoxy, 1-naphthyloxy, 2-naphthyloxy and the like.

The term "aryloxycarbonyl" as used herein refers to an aryloxy group, as defined above, attached via a carbonyl group including, but not limited to, phenyloxycarbonyl.

The term "guanidino" as used herein refers to a group of the structure —$NR^{105}C(=NR^{106})NR^{107}_2$. $R^{105}$, $R^{106}$, and $R^{107}$ are independently selected from hydrogen, alkyl, aryl, acyl, aryl—$SO_2$—, alkoxycarbonyl, arylalkoxycarbonyl, aryloxycarbonyl, or alkyl—$SO_2$—; where aryl, acyl, alkoxycarbonyl, arylalkoxycarbonyl, aryloxycarbonyl, and alkyl are as defined above. Alternatively, $R^{106}$, and $R^{107}$, taken together, may optionally be —$(CH_2)_{cc}$— wherein cc is an integer of from 2 to 6.

The term "halogen" as used herein refers to an atom selected from fluorine, chlorine, bromine and iodine.

The term "heterocyclic" as used herein, except where otherwise specified, refers to any aromatic or non-aromatic 5-, 6- or 7-membered ring or a bi- or tri-cyclic group comprising fused five- or six-membered rings having between one and three heteroatoms independently selected from oxygen, sulfur and nitrogen, wherein (i) each 5-membered ring has 0 to 2 double bonds and each 6- membered ring has 0 to 3 double bonds, (ii) the nitrogen and sulfur heteroatoms as well as the carbon atoms may optionally be oxidized by unsaturation and/or substitution by hydroxy, thiol, oxo or thiooxo, (iii) the nitrogen heteroatom may optionally be quaternized, (iv) any of the above heterocyclic rings may be fused to a benzene ring, and (v) any carbon or heteroatom with suitable valence may bear a substituent selected from $R^{111}$, $R^{112}$ and $R^{113}$, Representative heterocycles include, but are not limited to, pyrrolyl, pyrrolidinyl, pyrazolyl, pyrazolinyl, pyrazolidinyl, cytosinyl, thiocytosinyl, imidazolyl, imidazolinyl, imidazolidinyl, pyridyl, piperidinyl, pyrazinyl, piperazinyl, pyrimidinyl, pyridazinyl, xanthenyl, xanthonyl, xanthopterinyl, oxazoyl, oxazolidinyl, thiouracilyl, isoxazolyl, isoxazolidinyl, morpholinyl, indolyl, quinolinyl, uracilyl, urazolyl, uricyl, thiazolyl, thiazolidinyl, isothiazolyl, isothiazolidinyl, isoquinolinyl, thyminyl, benzimidazolyl, benzothiazolyl, benzoxazolyl, furyl, thienyl and benzothienyl.

The term "hydroxy-protecting group" as used herein refers to those groups which are known in the art to protect a hydroxyl group against undesirable reactions during synthetic procedures and to be selectively removable including, but not limited to, methylthiomethyl, tert-butyldimethylsilyl, tert-butyldiphenylsilyl, acyl unsubstituted or substituted with an aromatic group and the like.

The term "loweralkoxy" as used herein refers to a loweralkyl group, as defined below, attached to the remainder of the molecule via an oxygen atom.

The term "loweralkyl" as used herein refers to an alkyl group, as defined above, of 1 to 8 carbon atoms.

The terms "naturally occurring amino acid" and "standard amino acid" refer to an amino acid selected from the group consisting of alanine, arginine, asparagine, aspartic acid, cysteine, glutamine, glutamic acid, glycine, histidine, isoleucine, leucine, lysine, methionine, phenylalanine, proline, serine, threonine, typtophan, tyosine and valine.

The term "N-terminal protecting group" as used herein refers to those groups known in the art to protect the N-terminus against undesirable reactions during synthetic procedures or to prevent the attack of exopeptidases on the final compounds or to increase the solubility of the final compounds and includes, but is not limited to acyl, acetyl, pivaloyl, tert-butylacetyl, tert-butyloxycarbonyl (Boc), carbobenzyloxycarbonyl (Cbz), and benzoyl groups. Other such groups are described by Gross, E. and Meienhofer, J. in "The Peptides", Volume 3; Academic Press 1981.

The term "oxo" as used herein refers to an oxygen atom forming a carbonyl group.

The term "thiooxo" as used herein refers to a sulfur atom forming a thiocarbonyl group.

The term "pharmaceutically acceptable salts, esters, amides and prodrugs" as used herein refers to those carboxylate salts, amino acid addition salts, esters, amides and prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the slat thus formed. Representative salts include the hydrobromide, hydrochloride, sulfate, bisulfate, phosphate, nitrate, acetate, oxalate, valerate, oleate, palmitate, sterate, laurate, borate, benzoate, lactate, phosphate, tosylate, citrate, maleate, fumarate, succinate, tartrate, naphthylate, mesylate, glucoheptonate, lactiobionate and laurylsulphonate salts and the like. These may include cations based on the alkali and alkaline earth metals, such as sodium, lithium, potassium, calcium, magnesium and the like, as well as nontoxic ammonium, quaternary ammonium and amine cations including, but not limited to, ammonium, tetramethylammonium, tetraethylammonium, methylamine, dimethylamine, trimethylamine, triethylamine, ethylamine and the like. (See, for example S. M. Berg, et al., "Pharmaceutical Salts," *J. Pharm. Sci.*, 66: 1–19 (1977) which is incorporated herein by reference.)

Examples of pharmaceutically acceptable, non-toxic esters of the compounds of this invention include $C_1$ to $C_6$ alkyl esters wherein the alkyl group is a straight or branched chain. Acceptable esters also include $C_5$ to $C_7$ cycloalkyl esters as well as arylalkyl esters such as, but not limited to, benzyl. $C_1$ to $C_4$ alkyl esters are preferred. Esters of the compounds of the present invention may be prepared according to conventional methods.

Examples of pharmaceutically acceptable, non-toxic amides of the compounds of this invention include amides derived from ammonia, primary $C_1$ to $C_6$ alkyl amines and secondary $C_1$ to $C_6$ dialkyl amines wherein the alkyl groups are straight or branched chain. In the case of secondary amines the amine may also be in the form of a 5 or 6 membered heterocycle containing one nitrogen atom. Amides derived from ammonia, $C_1$ to $C_3$ alkyl primary amides and $C_1$ to $C_2$ dialkyl secondary amides are preferred. Amides of the compounds of the invention may be prepared according to conventional methods.

The term "prodrug" refers to compounds that are rapidly transformed in vivo to yield the parent compound of the above formula, for example by hydrolysis in blood. A thorough discussion is provided in T. Higuchi and V. Stella, "Pro-drugs as Novel Delivery Systems". Vol 14 of the A.C.S. Symposium Series, and in *Bioreversible Carries in Drug Desing*, ed. Edward B. Roche, American Pharmaceutical Association and Pergamon Press, 1987, both of which are incorporated herein by reference. Preferred prodrugs include:

(a) acyloxymethyl esters of carboxylic acids, for example, —C(O)—O—CH$_2$—O—C(O)—t—Bu, —C(O)—O—CH(CH$_3$)—O—C(O)—OCH$_2$CH$_3$ or —C(O)—O—Re wherein Re is

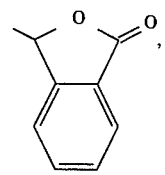

and the like:

(b) (5-methyl-2-oxo-1,3-dioxolen-4-yl)methyl esters of carboxylic acids:

esters derived from alcohol groups in the parent drug by reaction with sucinic acid, phosphoric acid, dialkylaminoacetic acid or an amino acid, for example, —O—C(O)—R$^f$ where R$^f$ is (CH$_3$)$_2$NCH$_2$—, NH$_2$CH$_2$—, n-PrNHCH$_2$—, NH$_2$CH$_2$CH$_2$—, (CH$_3$)$_2$NCH$_2$CH$_2$CH$_2$—, (CH$_3$)$_2$NCH$_2$CH$_2$—, N—morpholinylmethyl, N-methyl-N'-piperazinylmethyl, phenyl, CH$_3$CH$_2$CH$_2$—, CH$_3$CH$_2$CH$_2$CH$_2$— or HO(O)CCH$_2$CH$_2$—, and the like;

(d) N-Mannich bases of amides or amines, for example, —C(O)—NH—CH$_2$R$^c$ or —NH—CH$_2$R$^c$ wherein R$^c$ is piperidin-1-yl, morpholin-1-yl, N-phenethylamino, N-phenylpropanolamin, N-methylamino, N-ethylamino, N,N-diethylamino, N,N-dimethylamino, HO(O)C—CH(CH$_3$)—NH—, phenyl—NH—, phenyl—NH— or p—CH$_3$-phenyl—NH—, and the like, (e) N-hydroxymethyl derivatives of amides, for example, —C(O)—NH—CH$_2$OH;

(f) N-acyloxyalkyl derivatives of amides or heterocyclic amines, for example, —C(O)—NH—Rg or =N—Rg wherein Rg is acetoxymethyl, butyryloxymethyl, benzoyloxymethyl, nicotinoyloxymethyl, N,N—dimethylglycyloxymethyl, N,N-diethylglycyloxymethyl, N,N-dipropylgylcyloxymethyl, phenylalanyloxymethyl, leucyloxymethyl, phenylglycyloxymethyl or N,N-diethylalanyloxymethyl, and the like;

(g) oxazolidinones derived from ketone groups in the parent drug by reaction with 2-aminoethanol, N-methyl-2-aminoethanol, N-(2-hydroxyethyl)-2-aminoethanol, 2-aminopropanol, 2-amino-2-methylpropanol, 2-amino-2-hydroxymethylpropanol, 3-amino-2-hydroxypropane, 2-amino-1-phenylethanol, 3-aminopropanol or N-methyl-2-amino-1-phenylethanol, 3-aminopropanol or N-methyl-2-amino-1-phenylpropanol, and the like; and (h) enol esters derived from ketone groups in the parent drug, for example, acetyl enol esters, propionyl enol esters, butyryl enol esters, isobutyryl enol esters, pivaloyl enol esters, benzoyl enol esters or N,N-dimethylglycyl enol esters, and the like.

Where appropriate, prodrugs of derivatives of compounds of the present invention may be prepared by any suitable method. For those compounds in which the prodrug moiety is an amino acid or peptide functionality, the condensation of the amino group with amino acids and peptides may be effected in accordance with conventional condensation methods such as the azide method, the mixed acid anhydride method, the DCC (dicyclohexylcarbodiimede) method, the active ester method (p-nitrophenyl ester method, N-hydroxysuccinic acid imide ester method, ceyanomethyl ester method and the like), the Woodword reagent K method, the DCC-HOBT (1-hydroxy-benzotriazole) method and the like. Classical methods for amino acid condensation reactions are described in "Peptide Synthesis" Second Edition, M. Bodansky, Y. S. Klausner and M. A. Ondetti (1976).

As in conventional peptide synthesis, branched chain amino and carboxyl groups at alpha and omega positions in amino acids maybe protected and deprotected if necessary. The protecting groups for amino groups which can be used involve, for example, benzyloxycarbonyl (Z), o-chlorobenzyloxycarbonyl ((2-Cl)Z)), p-nitrobenzyloxycarbonyl (Z(NO$_2$)), p-methyoxybenzyloxycarbonyl (Z(OMe)), t-amyloxycarbonyl (Aoc), isobornealoxycarbonyl, adamantyloxycarbonyl (Adoc), 2-(4-biphenyl)-2-propyloxy carbonyl (Bpoc), 9-fluorenyl-methoxycarbonyl (Fmoc), methylsulfonylethoxy carbonyl (Msc), trifluoroacetyl, phthalyl, formyl, 2-nitrophenylsulfonyl (Nps), diphenylphosphinothioyl (Ppt) and dimethylphosphino-thioyl (Mpt).

The examples for protecting groups for carboxyl groups involve, for example, benzyl ester (OBzl), cyclohexyl ester, 4-nitrobenzyl ester (OBzlNO$_2$), t-butyl ester (OtBu), 4-pyridylmethyl ester (OPic) and the like.

In the course of the synthesis of certain of the compounds of the present invention, specific amino acids having functional groups other than amino and carboxyl groups in the branched chain such as arginine, cysteine, serine and the like may be protected, if necessary, with suitable protecting groups. It is preferably that, for example, the guanidino group (NG) in arginine may be protected with nitro, p-toluenesulfonyl (Tos), benzyloxycarbonyl (Z), adamantyloxycarbonly (Adoc), p-methoxybenzenesulfonyl, 4-methoxy-2, 6-dimethyl-benzenesulfonyl (Mts) and the like; the thiol group in cysteine may be protected with benzyl, p-methoxybenzyl, triphenylmethyl, acetamidomethyl, ethylcarbamyl, 4-methylbenzyl, (4-MeBzl), 2,4,6-trimethylbenzyl (Tmb) and the like; and the hydroxy group in serine may be protected with benzyl (Bzl), t-butyl, acetyl, tetrahydropyranyl (THP) and the like.

Numerous asymmetric centers exist in the compounds of the present invention. Except where otherwise noted, the present invention contemplates the various stereoisomers and mixtures thereof. Accordingly, whenever a bond is not represented by a bold or hashed line, it is intended that both steric orientations are intended.

The potent immunomodulatory activity which compounds of the instant invention demonstrate, in common in vitro biological assays, indicate that these compounds possess immunosuppressive, antimicrobial, antifungal, antiviral, antiinflammatory, and antiproliferative activity, and possess the ability to reverse chemotherapeutic drug resistance. While the compounds of the invention would be useful when used alone, combination therapy with other immunosuppressants, such as, FK506, rapamycin, cyclosporin A, picibanil, mycophenolic acid, azathioprine, prednisolone, cyclophosphamide, brequinar and leflunomide, would also be expected to be beneficial.

As immunosuppressants, the compounds of the present invention are useful when administered for the prevention immune-mediated tissue or organ graft rejection. Examples of transplanted tissues and organs which suffer from these effects are heart, kidney, liver, lung, small-bowel, and the like. The regulation of the immune response by the compounds of the invention would also find utility in the treatment of autoimmune diseases, such as rheumatoid arthritis, Hashimoto's thyroiditis, multiple scleroisis, myasthenia gravis, type I diabetes, uveitis, allergic encephalomyelitis, glomerulonephritis, and the like.

Further uses include the treatment and prophylaxis of inflammatory and hyperproliferative skin diseases and cutaneous manifestations of immunologically-mediated illnesses, such as psoriasis, atopical dermatitis, and *Epidermolysis bullosa*. Further instances where a compound of the invention would be useful include various eye diseases (autoimmune and otherwise) such as ocular pemphigus, Scleritis, and Graves' opthalmopathy, etc.

Other treatable conditions would include but are not limited to intestinal inflammations/allergies such as Crohn's disease and ulcerative colitis; renal diseases such as interstitial nephritis; skin diseases such as dermatomyositis; hematic diseases such as aplastic anemia, idopathic thrombocytopenic purpura, and autoimmune hemolytic anemia; circulatory diseases such as myocardosis; collagen diseases such as Wegener's granuloma; nephrotic syndrome such as glomerulonephritis; Pyoderma; Behcet's disease such as intestinal-, vasculo- or neuro-Behcet's disease, and also Behcet's which affects the oral cavity, skin, eye, vulva, articulation, epididymis, lung, kidney and so on. Furthermore, the compounds of the invention are useful for the treatment and prevention of hepatic disease such as immunogenic diseases (for example, chronic autoimmune liver diseases such as the group consisting of autoimmune hepatitis, primary biliary cirrhosis and sclerosing cholangitis), partial liver resection, acute liver necrosis (e.g., necrosis caused by toxin, viral hepatitis, shock or anoxia).

Aqueous liquid compositions of the present invention may be particularly useful for the treatment and prevention of various diseases of the eye such as autoimmune diseases (including, for example, conical cornea, keratitis, dysophia epithelialis corneae, leukoma, Mooren's ulcer, sclevitis and Graves' ophthalmopathy) and rejection of corneal transplantation.

Accordingly the pharmaceutical compositions of the present invention are those which comprise a therapeutically effective amount of a compound of the invention in combination a pharmaceutically acceptable carrier. Particular compositions are those which are useful for treating a patient for immune-mediated organ or tissue allograft rejection, a graft-versus-host disease, an autoimmune disease, a reversible obstructive airway disease, a hyperproliferative disease, or an ischemic or inflammatory intestinal or bowel disease.

Likewise, the methods of the present invention comprising treating a patient in need of immunosuppressive, antiinflammatory, antimicrobial, antifungal, antiviral or antiproliferative therapy, or requiring the reversal of chemotherapeutic drug resistance, by administering a therapeutically effective amount of a compound of the invention for such time and in such amounts as is necessary to produce the desired result.

When used in the above or other treatments, by "therapeutically effective amount" of one of the compounds of the present invention is meant a sufficient amount of the compound to treat a particular disorder, at a reasonable benefit/risk ratio. The compounds of the invention may be employed in pure form or, where such forms exist, in pharmaceutically acceptable salt, ester or prodrug form, Alternatively, the compound may be administered as pharmaceutical compositions containing the compound of interest in combination with one or more pharmaceutically-acceptable excipients. It will be understood, however, that the total daily usuage of the compounds and compositions of the present invention will be decided by the attending physician within the scope of sound medical judgment.

The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment;

drugs used in combination or coincidental with the specific compound employed; and like factors well known in the medical arts. For example, it is well within the skill of the art to start doses of the compound at levels lower than required for to achieve the desired therapeutic effect and to gradually increase the dosage until the desired effect is achieved.

The total daily dose of the compounds of this invention administered to a human or lower animal may range form about 0.001 to about 3 mg/kg/day. For purposes of oral administration, more preferably doses may be in the range of from about 0.005 to about 1.5 mg/kg/day. If desired, the effective daily dose may be divided into multiple doses for purposes of administration; consequently, single dose compositions may contain such amounts or submultiples thereof to make up the daily dose.

The pharmaceutical compositions of the present invention comprise a compound of the invention and a pharmaceutically acceptable carrier or excipient, which may be administered orally, rectally, parenterally, inracisternally, intravaginally, intraperitoneally, topically (as by powers, ointments, drops or transdermal patch), bucally, or as an oral or nasal spray. By "pharmaceutically acceptable carrier" is meant a non-toxic solid, semi-solid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some case, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar—agar, calcium carbonate, potato or tapico starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearae, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as filler sin soft and hard-filled gelatin capsules using such excipients as lactose or milk sugar as well as high molecular weight polyethylene glycols and the like.

The solid dosage forms of tablets, dragees, capsules, pills, and granules can be prepared with coating and shells such as enteric coatings and other coatings well known in the pharmaceutical formulating art. They may optionally contain opacitying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar—agar, and tragacanth, and mixtures thereof.

Topical administration includes administration to the skin or mucosa, including surfaces of the lung and eye. Compositions for topical administration, including those for inhalation, may be prepared as a dry powder which may be pressurized or non-pressurized. In non-pressurized powder compositions, the active ingredient in finely divided form may be used in admixture with a larger-sized pharmaceutically acceptable inert carrier comprising particles having a size, for example, of up to 100 micrometers in diameter. Suitable inert carriers include sugars such as lactose. Desirably, at least 95% by weight of the particles of the active ingredient have an effective particle size in the range of 0.01 to 10 micrometers.

Alternatively, the composition may be pressurized and contain a compressed gas, such as nitrogen or a liquefied gas propellant. The liquefied propellant medium and indeed the total composition is preferably such that the active ingredient does not dissolve therein to any substantial extend. The pressurized composition may also contain a surface active agent. The surface active agent may be a liquid or solid non-ionic surface active agent or may be a solid anionic surface active agent. It is preferred to use the solid anionic surface active agent in the form of a sodium salt.

A further form of topical administration is to the eye, as for the treatment of immune-mediated conditions of the eye such as autoimmune diseases, allergic or inflammatory conditions, and corneal transplants. The compound of the invention is delivered in a pharmaceutically acceptable ophthalmic vehicle, such that the compound is maintained in contact with the ocular surface for a sufficient time period to allow the compound to penetrate the corneal and internal regions of the eye, as for example the anterior chamber, posterior chamber, vitreous body, aqueous humor, vitreous humor, cornea iris/ciliary, lens, choroid/regina and sclera. The pharmaceutically acceptable ophthalmic vehicle may, for example, be an ointment, vegetable oil or an encapsulating material.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefor melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic. Methods to form liposomes are known in the art. See, for example, Prescott, Ed., *Methods in Cell Biology*, Volume XIV, Academic Press, New York, N.Y. (1976), p. 33 et seq.

The compounds of the invention may be prepared using one or more of the processes which follow. The starting materials for use in these processes are preferably one of the macrolides isolated from culture media obtained in accordance with known methods by fermentation of microorganisms of the genus Streptomyces, which are disclosed in European Patent Application No. 0184162. Samples are available from the Fermentation Research Institute, Tsukuba, Ibaraki 305, Japan under the provisions of the Budapest Treaty, under deposit No. FERM BP-927. This strain has been redeposited on Apr. 27, 1989 with the Agricultural Research Culture Collection International Depository, Peoria, Ill. 61604, USA under the provisions of the Budapest Treaty, under deposit No. NRRL 18488. The macrolide FR-900520 (European Patent Application 0184162), also known as ascomycin, may be prepared in accordance to the published methods of (i) H. Hatanaka, M. Iwami, T. Kino, T. Goto and M. Okuhara, FR-900520 and FR-900523, Novel immunosuppressants isolated from *A streptomyces. I. Taxonomy* of the producing strain. *J. Antibiot.*, 1988. XLI (11), 1586–1591; (ii) H. Hatanaka, T. Kino, S. Miyata, N. Inamura, A. Kuroda, T. Goto, H. Tanaka and M. Okuhara, FR-900520 and FR-900523, Novel immunosuppressants isolated from *A streptomyces*. II. Fermentation, isolation and physico-chemical and biological characteristics. *J. Antibiot.*, 1988. XLI(11), 1592–1601; (iii) T. Arai, Y. Koyama, T. Suenaga and H. Honda, *Ascomycin, An Antifungal Antibiotic, J. Antibiot.*, 1962. 15(231–2); and (iv) T. Arai in U.S. Pat. No. 3,244,592. One or more of the processes discussed below may be then employed to produce the desired compound of the invention.

Such processes comprise:

(a) producing a compound of formula I, which contains a CH—OR group, by selective activation of a selected CH—OH group in a corresponding compound wherein —OR is a leaving group which is easily displaced by nucleophilic attack.

(b) producing a compound of formula I, which contains a R—OCOR$^{10}$ group, by selective acylation of a R—OH group in a corresponding compound where in R$^{10}$ is as defined above.

(c) producing a compound of formula I, which contains a CH—O—P(O)(OR$^{10}$)$_2$ group, by selective phosphorylation of a CH—OH group in a corresponding compound wherein R$^{10}$ is as defined above.

(d) producing a compound of formula I, which contains a CH—O—C(=S)—OR$^{10}$ group, by selective aryl-, arylalkyl- or alkyloxythiocarbonylation of a CH—OH group in a corresponding compound wherein R$^{10}$ is as defined above.

(e) producing a compound of formula I, which contains a C(OH)=CH—C(=O) or a C(=O)—CH$_2$—C(=O) group, by selective oxidation of a CH(OH)—CH$_2$—C(=O) group in a corresponding compound.

(f) producing a compound of formula I, which contains a C(OCOR$^{10}$)=CH—C(=O) group, by selective O-acylation of a C(OH)=CH—C(=O) or a C(=O)—CH$_2$—C(=O) group in a corresponding compound wherein R$^{10}$ is as defined above.

(g) producing a compound of formula I, which contains a carbon—carbon double bond, by elimination of HL from a corresponding compound, where L is a leaving group.

(h) producing a compound of formula I, which contains one or more hydroxyl groups, by selective reduction of one or more C=O groups of a corresponding compound.

(i) producing a compound of formula I, which contains one or more carbonyl groups, by selective oxidation of one or more hydroxyl groups of a corresponding compound.

(j) producing a compound of formula I, which contains an oxime group, by selective reaction of one of the carbonyl groups of a corresponding compound with hydroxyl amine or O-alkylated hydroxyl amines.

(k) producing a compound of formula I, which contains a pyrazole system, by condensation of a 1,3-dicarbonyl group of a corresponding compound and appropriate hydrazines.

(l) producing a compound of formula I, which contains an isoxazole system, by condensation of the 1,3-dicarbonyl group of a corresponding compound with hydroxyl amine.

(m) producing a compound of formula I, which contains a hydrazone or semicarbazone, by selective hydrazone formation with a corresponding ketone.

(n) producing a compound of formula I, which contains an allylic alcohol, by selective reduction of a corresponding enone.

(o) producing a compound of formula I, which contains an epoxide, by selective addition of the carbene arising form diazomethane across an activated carbonyl.

(p) producing a compound of formula I, which contains a carboxylic acid, by selective ester cleavage in a corresponding compound.

(q) producing a compound of formula I, which contains a substituted or unsubstituted carboxamide, by selective condensation of the corresponding amine with a corresponding carboxylic acid.

(r) producing a compound of formula I, which contains a 24R-hydroxyl substituent, by selective inversion of the naturally occurring 24S configuration.

(s) producing a compound of formula I, which contains a tertiary alcohol, by selective addition of a Gringard reagent or an organometallic reagent to a carbonyl moiety of a corresponding compound.

(t) producing a compound of formula I, which contains a $CH_2$ group, by selective reduction of a 1,2-dicarbonyl or masked 1,2-dicarbonyl group of a corresponding compound.

(u) producing a compound of formula I, which contains one ethanal yl group, first by selective oxidation of the double bond of an allyl group to a vicinal diol, followed by oxidative cleavage of the diol in a corresponding compound.

(v) producing a compound of formula I, which contains one carboxymethyl group, by selective oxidation of an ethanalyl group in a corresponding compound, (w) producing a compound of formula I, which contains one alkyl carboxymethyl group, by esterification of a carboxymethyl group in a corresponding compound, (x) producing a compound of formula I, which contains one cyclopropylmethyl group, by selective cyclopropanation of the double bond of an allyl group in a corresponding compound, (y) producing a compound of formula I, which contains one methyl ketone, by selective oxidation of the double bond of an allyl group in a corresponding compound, (z) producing a compound of formula I, which contains an alpha, beta-saturated ketone, by reduction of the corresponding alpha, beta-unsaturated enone, (aa) producing a compound of formula I, which contains a substituted or unsubstituted piperazine, by treatment of an enone system with a piperazine resulting in a Michael addition at the beta-carbon, (bb) producing a compound of formula I, which contains a group —CHOC(O)NHR$^{24}$, where R$^{24}$ is as defined above, by selective carbamate formation from a selected —CHOH group in a corresponding compound.

(cc) producing a compound of formula I, which contains a —CHOC(O)OR$^{10}$, where R$^{10}$ is as defined above, by selective aryl-, arylalkyl-, or alkyloxycarbonylation of a —CHOH group in a corresponding compound.

(dd) producing a compound of formula I, which contains an allylic hydroxyl group, by selective oxidation of an allylic methylene group in a corresponding compound.

(ee) producing a compound of formula I, which contains either an alpha-hydroxy, beta-keto acid or ester, by selective nucleophilic addition and subsequent benzilic acid type rearrangement of a corresponding compound containing a tricarbonyl moiety.

(ff) producing a compound of formula I, which contains a 1,2-dicarbonyl system, by selective oxidative cleavage of a benzilic acid rearrangement product which has been derived from a corresponding compound.

(gg) producing a compound of formula I, which contains a CH—O—C(=NH)CCl$_3$ group, by selective trichloroacetylimidation of a CH—OH group in a corresponding compound.

In process (a), suitable reagents for activation of an alcohol include acetic anhydride, trifluoromethanesulfonic anhydride (triflic anhydride), methanesulfonyl chloride (mesyl chloride), p-toluenesulfonyl chloride (tosyl chloride), trifluoroacetic anhydride, trifluoroacetyl chloride, methoxysulfonyl fluoride (magic methyl), o-nitrobenzenesulfonyl chloride, 1-methyl-2-fluoropyridinium salt and the like.

The activation may be carried out in a solvent which does not adversely affect the reaction (e.g., diethylether, dichloromethane, tetrahydrofuran, chloroform or N,N-diemthylformamide or a mixture thereof). The reaction may require cooling or heating, depending on the activation method chosen. Further, the reaction is preferably conducted in the presence of an organic or inorganic base such as an alkaline earth metal (e.g. calcium, etc.), alkali metal hydride (e.g. sodium hydride, etc.), alkali metal hydroxide (e.g. sodium hydroxide, potassium hydroxide, etc.), alkali metal carbonate (e.g. sodium carbonate, potassium carbonate, etc.), alkali metal hydrogen carbonate (e.g. sodium hydrogen carbonate, potassium hydrogen carbonate, etc.), alkali metal alkoxide (e.g. sodium methoxide, sodium ethoxide, potassium tert-butoxide, etc.), alkali metal alkanoic acid (e.g. sodium acetate, etc.), trialkylamine (e.g. triethylamine, etc.), pyridine compounds (e.g. pyridine, lutidine, picoline, 4-N,N-dimethylaminopyridine, etc.), quinoline, and the like, preferably in the presence of organic bases such as triethylamine or pyridine.

The activation may also be carried out using a starting material having an opposite configuration at a carbon center. In this situation, the following two additional steps are required to yield a starting material having an epimeric hydroxyl moiety, i.e. (1) the alcohol is oxidixed to its corresponding ketone, (2) the obtained ketone is reduced under selective conditions. Both chiral centers having either [R]- or [S]-configuration can be obtained selectively and separately.

In process (b), suitable O-acylations may be carried out using the methods of symmetric carboxylic acid anhydrides, carboxylic acid halides, mixed carbonic-carboxylic anhydrides, active esters (p-nitrophenylester, trichlorophenyl ester, pentafluorophenyl ester, N-hydroxysuccinimide, cyanoethyl and the like), and carboxylic acid with suitable condensing reagents such as DCC (N,N-dicyclohexylcarbodiimide and its related condensing agents), DCC-HOBt (N,N-dicyclohexylcarbodiimide-1-hydroxybenzotriazole), Woodward reagent K method, N,N-carbonyldiimidazole and phosphonium containing reagents (e.g. benzotriazolyloxytris[dimethylamino]phosphonium hexafluorophosphate, N,N-bis[2-oxo-3-ox-azolidinyl]phosphorodiamidic chloride, diethylphosphorobromidate, diphenylphosphoryl azide, bromo tris[dimethylamino]phosphonium hexafluorophosphate, and the like). Suitable reagents for ester formation include, but are not limited to formyl derivatives, acetyl halides (chloroacetyl, trichloroacetyl, o-nitrophenylacetyl, o-nitrophenoxyacetyl, acetoacetyl, [N'-dithiobenzyloxycarbonylamino]acetyl and the like), and substituted propionyl derivatives (3-phenylpropionyl, isobutyryl, picolinoyl, and the like). 4-Dimethylaminopyridine is often used to catalyze the reaction. Other groups may be found in volume 3 of *The Peptides* Gross, E. and Meinhofer, J. Academic Press, 1981 and *Protective Groups in Organic Synthesis* Greene, T. W. John Wiley & Sons, New York, Chapter 7, 1981. Typically used coupling conditions are described by Gross, E.; Meinhofer, J. *"The Peptides"* vol. 3, Academic Press, 1981. The O-acylation may be carried out in a solvent which does not adversely affect the reaction (e.g. acetong, dichloromethane, chloroform, tetrahydrofuran, N,N-dimethylformamide, dimethylsulfoxide, diethylether, and the like, or a mixture thereof). The reaction may be conducted above, at, or below ambient temperature. Alternatively, metal salts may be formed from the desired alcohols and then condensed with an ester which may or may not be activated.

In process (c), phosphorylation may be carried out using, but is not limited to the 2-halo-2-oxo-1,3,2-dioxaphospholane-triethylamine reaction (Chandrarakumar, N. S.; Hajdu, J. *J. Org. Chem.* 1983, 48, 1197) The phosphorylation may be carried out in a solvent which does not adversely affect the reaction (e.g., benzene, toluene, acetone, dichloromethane, tetrahydrofuran or N,N-dimethylformamide or a mixture thereof). Further, the reaction is preferably conducted in the presence of organic or inorganic bases, as described in process (a), preferably in the presence of organic bases such as triethylamine, pyridine etc. The reaction may be conducted above, at, or below ambient temperature, more preferably from 0° to 50° C.

In process (d), aryl- or alkyloxythiocarbonylation may be carried out using aryl- or alkyloxythiocarbonylchloride or corresponding halides in the presence of suitable tert-amines such as trialkylamine, pyriding, and the like. The aryl- or alkythiocarbonylation may be carried out in a solvent which does not adversely affect the reaction (e.g. acetone, dichloromethane, tetrahydrofuran, pyridine, N,N-dimethylformamide etc. or a mixture thereof). The reaction may be conducted above, at, or below ambient temperature.

In process (e), suitable oxidizing reagents include activated dialkyl sulfoxides (e.g. dimethylsulfoxide, methylethylsulfoxide) (Mancuso, A. J.; Swern, D. *Synthesis* 1981, 165), organo chromates [e.g. pyridinium chlorochromate (Corey, E. J.; Suggs, J. W. *Tetrahedron Lett.* 1975, 2647; Corey, E. J.; Boger, D. L. *Tetrahedron Lett.* 1978, 2461), pyridinium dichromate (Corey, E. J.; Schmidt, G. *Tetrahedron Lett.* 1979, 5,399), Collins reagent (Collins, J. C.; Hess, W. W.; Frank, F. J. *Tetrahedron Lett.* 1968, 3363)], tetrapropylammonium perruthenate (Griffith, W. P.; Ley, S. V.; Whitcombe, G. P.; White, A. D. *Chem. Commun.* 1987, 1625; Griffith, W. P. *Aldrichimica Acta.* 1990, 23, 13), and the like. The oxidation may be carried out in a solvent which does not adversely affect the reaction (e.g. acetone, dichloromethane, tetrahydrofuran, pyridine, N,N-dimethylformamide, etc. or a mixture thereof). The reaction may be conducted above, at, or below ambient temperature.

In process (f), suitable O-acylation reagents include, but are not limited to alkyl, aryl, or arylalkyl acyl halides (Lakhvich, F. A.; Khlebnicova, T. S.; Akhrem, A. A. *Synthesis* 1985, 8, 784). The O-acylation may be carried out in a solvent which does not adversely affect the reaction (e.g. acetone, dichloromethane, tetrahydrofuran, pyridine, N,N-dimethylformamide, etc., or a mixture thereof). The reaction may be conducted above, at, or below ambient temperature.

In process (g), L may be hydroxy, or a good leaving group (halogen, tosylate, mesylate or triflate, for example). When a precursor compound contains a C(OH)—$CH_2$—C=O group, the elimination of $H_2O$ may be carried out in a solvent which is inert under the reaction conditions (e.g. toluene) with a trace of acid (e.g. toluenesulfonic acid), at a temperature selected from 50° to 100° C. When the precursor compound contains a good leaving group, the elimination may be carried out in the presence of a base (e.g. triethyl amine or potassium carbonate), at a temperature selected from 0° to 100° C.

In process (h), suitable reagents include sodium borohydride, zinc in acetic acid, sodium triacetoxyborohydride in acetic acid, lithium trialkoxyaluminum hydride in tetrahydrofuran, potassium or lithium tri-sec-butylborohydride in tetrahydrofuran, and borane/t-butylamine complex in a solvent such as methanol or ethanol. The reduction may be conducted at −70° C. to room temperature.

In process (i), the reagent to be used in this reaction may include di(lower)alkyl sulfoxide (e.g. dimethyl sulfoxide, ethyl methyl sulfoxide, propyl methyl sulfoxide, isobutyl methyl sulfoxide, butyl methyl sulfoxide, isobutyl methyl sulfoxide, hexyl methyl sulfoxide, etc). This reaction is usually conducted in the presence of oxalyl chloride, acid chlorides, lower alkanoic anhydride such as acetic anhydride in a conventional solvent that does not adversely influence the reaction such as dichloromethane, acetone, ethyl acetate, tetrahydrofuran, pyridine, N,N-dimethylformamide, etc., followed by the addition of a tertiary amine (e.g. triethyl amine). The reaction may be conducted at −70° C. to room temperature.

In process (j), suitable oxygen-substituted amines include hydroxyl amine, O-alkylhydroxyl amines, and O-arylalkyl hydroxyl amines, for example O-benzyl hydroxyl amine. Suitable solvents include those that doe not adversely affect the reaction, for example ethanol or methanol. The reaction is preferably carried out with one equivalent of hydroxyl amine, and at a temperature of 25° to 100° C., more preferably at the reflux temperature of the solvent.

In process (k), suitable hydrazines include alkylhydrazines (e.g. butylhydrazine), arylhydrazines (e.g. phenylhydrazine), acylhydrazines (e.g. acetylhydrazine), semicarbazides (e.g. t-butyloxycarbonyl hydrazine) and sulfonyl hydraziens (e.g. tosy hydrazine) in a conventional solvent that does not adversely affect the reaction such as tetrahydrofuran, methanol or ethanol. The reaction may be conducted at 20° to 100° C.

In process (l), one equivalent of hydroxyl amine hydrochloride and teritiary amine (e.g. N-methylmorpholine) in a conventional solvent that does not adversely affect the reaction such as tetrahydrofuran, methanol, ethanol or isopropanol is used to prepare the compound. The reaction is conducted at 20° to 100° C.

In process (m), an aryl- or alkylsulfonyl hydrazone may be formed by treatment of a ketone with an aryl- or alkylsulfonyl hydrazide in the present of an acid catalyst in a solvent suitable for the reaction such as methanol or ethanol at temperatures ranging from ambient to the reflux temperature of the solvent.

In process (n), an allylic alcohol may be produced by selective reduction of an alpha-beta unsaturated enone. This is accomplished with but not limited to sodium borohydride in the presence of cerium(III) chloride heptahydrate in a suitable solvent such as methanol at or near 0° C.

In process (o), an epoxide may be produced on the central caarbonyl of a tricarbonyl moiety by but not limited to excess diazomethane as described in: Fisher, M. J.; Chow, K.; Villalobos, A.; Danishefsky, S. J. *J. Org. Chem.* 1991, 56, 2900–2907.

In process (p), liberation of the ester to the acid may be achieved by the cleavage of a suitable substituted ester function. Such a functional group may be benzyl, 2,2,2-trichloroethyl, 9-fluorenylmethyl and the like. These are cleaved by methods well known to those skilled in the art.

In process (q), condensation of an amine with the acid may be performed using the mixed or symmetrical anhydride of said acid, or an ester of the acid, preferably activated, such as the ester derived from hydroxybenzotriazole, or the corresponding acylcyanide, acylimidazole, or acylazide of the aforementioned acid.

In process (r), selective protection of the 32-hydroxyl moiety may be achieved using one of a variety of trialkylsilyl groups. This then leaves exposed a lone secondary alcohol on C-24 for selective inversion, which may be accomplished by activation of the 24- hydroxy as a mesylate, tosylate, etc., followed by inversion with a suitable nucleophile such as water, benzoic acid, formic acid, etc. On the other hand inversion of the unactivated 24-hydroxy group may be achieved using well described Mitsunobu conditions. Liberation of the silyl ether and inverted C-24 acylated hydroxy (if carboxylic acids are used as the nucleophile) is accomplished using methods well known to those skilled in the art. Alternatively, inversion may be accomplished without protection of the 32-hydroxyl group if ascomycin, FK506, or similar compounds are treated with diethylaminosulfur trifluoride (DAST) in an inert solvent such as methylene chloride.

In process (s), the organometallic reagent may be a Gringard reagent, an alkyllithium, or an aryllithium reagents.

The selective addition may be carried out in a solvent which does not adversely affect the reaction (e.g., hexanes, ether, tetrahydrofuran, dimethoxyethane or 2-methoxyethyl ether). The reaction may be carried out in the presence of cerium (III) at a temperature selected from $-100°$ C. to $0°$ C.

In process (t), the reduction of a 1,2-dicarbonyl group of a corresponding compound may be carried out in a solvent which does not adversely affect the reactions (e.g., methanol, ethanol, ethanol, pyridine or N,N-dimethylformamide).

The reducing agents used may be tin amalgam, aluminum amalgam with hydrogen chloride in ethanol, or may be hydrogen sulfide in a pyridine or N,N-dimethylformamide.

In process (u), suitable reagents for vicinal hydroxylation include osmium tetraoxide, potassium permanganate, and iodine in conjunction with silver acetate. Osmium tetroxide is preferably used with a regenerating agent such as hydrogen peroxide, alkaline t-butyl hydroperoxide or N-methyl-morpholine-N-oxide, and a solvent that does not adversely affect the reaction, for example diethyl ether or tetrahydrofuran. Potassium permanganate is preferably used in mild conditions, for example alkaline aqueous solution or suspensions. Co-solvents such as t-butanol or acetic acid may also be used. Iodine-silver acetate under 'wet' conditions yields cis-diols. Preferably, iodine is used in aqueous acetic acid in the presence of silver acetate. Iodine-silver acetate under 'dry' conditions yields trans-diols. Here, the initial reaction is carried out in the absence of water, and final hydrolysis yields the diol. In each case, the oxidation is preferably carried out at a temperature of $0°$ to $100°$ C.

Suitable regions for the oxidative cleavage of the vicinal diol include lead tetraacetate, phenyliodoso acetate, periodic acid or sodium metaperiodate. Suitable solvents for the first two reagents include benzene and glacial acetic acid. The second two reagents are preferably used in aqueous solution. The reaction is preferably carried out at a temperature of $0°$ to $100°$ C.

In process (v), suitable reagents for the oxidation of an aldehyde of the corresponding compound may include silver oxide, chromic acid and potassium permanganate. In the presence of a variety of catalysts, oxygen may also be used in converting an aldehyde to a carboxylic acid of a corresponding compound. The catalysts may be palladium or platinum oxide. The air oxidation may be carried out in a solvent which does not adversely affect the reaction (e.g., ethanol, water, acetonitrile, aqueous acetone or pyridine) at a temperature of $0°$ to $100°$ C.

In process (w), esters of a corresponding carboxylic acid may be prepared under neutral conditions at room temperature by the reaction of the carboxylic acid with alcohols in the presence of molar amounts of activating reagents such as triphenyl phosphine and diethyl azodicarboxylate, carboximides, N,N'-carbonyldiimidazole and 1-methyl-2-halopyridinium iodide. Esters may also be formed by reacting the corresponding carboxylic acid with diazoalkanes in a solvent which does not adversely affect the reaction (e.g., ether, tetrahydrofuran or methylene chloride) at a temperature of from $0°$ to $100°$ C.

In process (x), the cyclpropanation of the allyl group of a corresponding compound may be carried out with diazoalkanes in a solvent which does not adversely affect the reaction (e.g., ether, methylene chloride or tetrahydrofuran) in the presence of a catalyst such as palladium (II) acetate. The temperature of the reaction is of $-15°$ to $5°$ C.

In process (y), suitable reagents include air, a palladium (II) halide (e.g. palladium (II) chloride), in conjunction with a cuprous halide (e.g. cupper (I) chloride). Suitable solvents include those that do not adversely affect the reaction (e.g. DMF and water). The reaction is preferably carried out at a temperature of $0°$ to $100°$ C.

In process (z), reduction of an enone to the corresponding saturated ketone may be accomplished with but not limited to hydrogenation with a suitable catalyst such as either palladium on carbon or thodium on alumina in a solvent inert to the reaction conditions (e.g. methanol, ethanol, ispropanol, ethyl acetate) in a temperature range from $-78°$ to $100°$ C.

In process (aa), the piperazine is added to an enone in a solvent which does not adversely affect the reaction (e.g., hexanes, ether, tetrahydrofuran, dimethoxyethane or 2-methoxyethyl ether, dichloromethane) in the presence of an organic base such as triethylamine. The reaction may be carried out at a temperature selected from $-20°$ C. to $100°$ C.

In process (bb), carbamate formations may be carried out by reacting CH—OH group with appropriate isocyanates, or an appropriate compound containing an amino functional group derivative activated with N,N-carbonyldiimidazole, N,N-carbonyl-bis-(N-methylimidazole triflate), phosgene, diphosgene or triphosgene in the presence of a tert-amine. Alternatively, the CH—OH group may be activated with N,N-carbonyldiimidazole, phosgene, diphosgene or triphosgene in the presence of a tert-amine. The activated CH—OH group derivative may then reacted with appropriate amino-containing compound to produce the carbamate. The carbamate formation may be carried out in a solvent which does not adversely affect the reaction (e.g. acetone, toluene, dichloromethane, tetrahydrofuran, N,N-dimethylformamide, etc. or a mixture thereof). The reaction may be conducted above, at, or below room temperature. The literature for the preparation of carbamates may be found in volume 3 of *The Peptides*, Gross, E. and Meinhofer, J. Academic Press, 1981 and *Protective Groups in Organic Synthesis*, 2nd Ed., Greene, T. W. John Wiley & Sons, New York, p. 315, 1991.

In process (cc), aryl-, heterocyclic-, or alkyloxycarbonylation may be carried out using aryl-, heterocyclic-, or alkyl-chloroformate in the presence of amines like triethylamine, diisopropylethylamine, pyridine and the like. Alternatively, the reaction may be carried out by reacting the corresponding aryl-OH, heterocyclic-OH or alkyl-OH with —CHOC(O)Cl or —CHOC(O)-(p-nitrophenyl) in a corresponding compound in the presence of amine base. The reaction may be carried out in a solvent which does not adversely affect the reaction (e.g. acetone, dichloromethane, tetrahydrofuran, pyridine and N,N-dimethylformamide, or a mixture thereof). The reaction may be conducted above, at or below ambient temperature.

In process (dd) allylic oxidations may be carried out using selenium dioxide with or without a co-oxidant, such as tert-butyl hydroperoxide, in an inert solvent such as tetrahydrofuran, ether, ethylacetate, water, or a combination thereof. The reaction may be conducted at room temperature to 100° C.

In process (ee), a benzilic acid rearrangement to yield an alpha-hydroxy acid may be initiated in a tricarbonyl system by treatment with a slight excess of a hydroxylic base in THF-water initially between 0° C. and room temperature. The temperature may be permitted to rise to room temperature during the course of the reaction. Other nucleophiles such as methanol are also for this type of transformation at temperatures from ambient to the reflux temperature.

In process (ff), an alpha-hydroxy acid may be oxidatively cleaved by treatment with lead tetraacetate in an inert solvent (e.g. benzene) to form a ketone.

In process (gg), trichloroacetylimidate formation may be carried out using, but not limited to trichloroacetonitrile the presence of base (Becker, D. and Galili, N. *Tetrahedron Lett.*, 1992, 33, 4775–4778; Gurjar, M. K. and Saha, U. *ibid.*, 1992, 33, 4979–4982; Zimmermann, P.; Bommer, R.; Bar, T. and Schmidt, R. R. *J. Carbohyd. Chem.*, 1988, 7, 435–452). Suitable base for the reaction include cesium carbonate, 1,8-diazobicyclo[5.4.0]undec-7-ene, 1,5-diazobicyclo[4.3.0]non-5-ene and the like. This reaction may also carried out by transformation of trichloroacetylimidate moiety from other alcohol in the presence of Lewis acid. Suitable Lewis acid for the reaction include boron trifluoride etherate, zinc chloride, zinc iodide, titanium tetrachloride and the like. Other acids may also be used for this reaction. Such acids are trifluorosulfonic acid, p-toluene sulfonic acid, camphor sulfonic acid and the like.

The reaction may be carried out in a solvent which does not adversely affect the reaction (e.g., diethylether, dichloromethane, tetrahydrofuran, chloroform or N,N-dimethylformamide or a mixture thereof). The reaction may require cooling or heating, depending on the activation method chosen. The reaction is usually conducted under from cooling to heating, preferably from −70° C. to 50° C. The reaction may require 20 minutes to one day, depend on the reagent and temperature chosen.

The compounds, processes and uses of the present invention will be better understood in connection with the following examples, which are intended as an illustration of and not a limitation upon the scope of the invention. Both below and throughout the specification, it is intended that citations to the literature are expressly incorporated by reference.

EXAMPLE 1

Formula I: R=ethyl; $R'=R^2=R^4=R^5=R^9$=H; n=1; $R^3$=OCH$_3$; $R^1$=C$_6$H$_5$OC(S)O (R Configuration); $R^6$ and $R^7$ taken together are oxo; $R^8$=OH; Y=subformula Ia, wherein $R^{18}=R^{19}=R^{21}$=H; $R^{20}$=OH; $R^{22}$ and $R^{23}$ taken together are oxo, Ascomycin (988.8 mg, 1.25 mmol) was dissolved in 10 mL of methylene chloride in an ice bath. Pyridine (404 uL, 5 mmol) followed by phenoxythiocarbonyl chloride (190 uL, 1.375 mmol) were added. The mixture was stirred at 0° C. for 5 min and allowed to stir at room temperature for 24 hours. Additional pyridine (404 uL, 5 mmol) and phenoxythiocarbonyl chloride (190 uL, 1.375 mmol) were added, and stirring was continued for 4 hours. Solvents were evaporated and 40 mL of ethyl acetate was added to the residue. The ethyl acetate layer was washed with 10%-KHSO$_4$ (3×), brine, and dried overanhydrous magnesium sulfate. Evaporation of the solvent gave 1.400 g of crude product which was purified by silica gel column chromatography, eluting with 5%-ethyl acetate in chloroform. The title compound (730 mg) was obtained. MS (FAB) m/z: M+K=966; IR(KBr) 3420, 2980, 2930, 2870, 2825, 1740, 1705, 1645, 1630, 1590, 1490, 1450, 1375, 1365, 1320, 1280, 1260, 1230, 1200, 1175, 1140, 1100, 1090, 1080, 1035, 1020, 1005 cm$^{-1}$.

EXAMPLE 2

Formula I: R=ethyl; $R'=R^2=R^4=R^5=R^9$=H; n=1; $R^3$=OCH$_3$; $R^1$=C$_6$H$_5$OC(S)O (R Configuration); $R^6$ and $R^7$ taken together are oxo; $R^8$=OH; Y=subformula Ia, wherein $R^{18}=R^{19}=R^{21}$=H; $R^{20}$=C$_6$H$_5$OC(S)O; $R^{22}$ and $R^{23}$ taken together are oxo.

The title compound (460 mg) was isolated from the reaction described in Example 1 as a minor product. MS (FAB) m/z: M+K=1103; IR(KBr) 3420, 2980, 2930, 2870, 2820, 1740, 1710, 1645, 1620, 1590, 1490, 1450, 1380, 1365, 1320, 1280, 1260, 1210, 1200, 1140, 1100, 1070, 1035, 1015, 1000 cm$^{-1}$.

EXAMPLE 3

Formula I: R=ethyl; $R'=R^2=R^4=R^5=R^9$=H; n=1; $R^3$=OCH$_3$; $R^1$=OH (R Configuration); $R^6$ and $R^7$ taken together are oxo; $R^8$=OH; Y=subformula Ia, wherein $R^{18}=R^{21}$=H; $R^{19}$ and $R^{20}$ taken together form a bond; $R^{22}$ and $R^{23}$ taken together are oxo. The title compound was prepared according to the methods described in the published European Patent Application No. 89192668 of Fisons, P.26, Example 11: mp 124°–125° C., MS (FAB) m/z: M+NH$_4$=791.

EXAMPLE 4

Formula I: R=ethyl; $R'=R^4=R^5=R^9$=H; n=1; $R^3$=OCH$_3$; $R^1$ and $R^2$ taken together are oxo; $R^6$ and $R^7$ taken together are oxo; $R^8$=OH; Y=subformula Ia, wherein $R^{18}=R^{19}=R^{21}$=H; $R^{20}$=OH; $R^{22}$ and $R^{23}$ taken together are oxo. Methylsulfide-chlorine complex was prepared by adding oxalyl chloride (0.32 g) into a stirred solution of dimethylsulfoxide (0.44 g) in methylene chloride (4 mL) and stirring at −70° C. for 0.5 hours. The solution of the complex was added in slow dropwise fashion into a stirring solution of ascomycin (1.6 g) in methylene chloride (5 mL) at −70° C. After stirring for 0.25 hours, triethylamine (1.4 g) was added at −70° C. Stirring was continued at −70° C. for 0.5 hours and then at room temperature for 1 hour. The reaction mixture was then diluted with ether (100 mL), washed with 1N HCl (aq) (2×30 mL), saturated brine (30 mL), dried over magnesium sulfate and solvent removed. The product was purified on silica gel (70 g) with ether elution. Yield: 0.95 g; MS (FAB) m/z: M+H=790.

EXAMPLE 5

Formula I: R=ethyl; R'=$R^2$=$R^4$=$R^5$=$R^9$=H; n=1; $R^3$=$OCH_3$; $R^1$=t-Bu$(CH_3)_2$SiO— (R Configuration); $R^6$ and $R^7$ taken together are oxo; $R^8$=OH; Y=subformula Ia, wherein $R^{18}$=$R^{19}$=$R^{21}$=H; $R^{20}$=t-Bu$(CH_3)_2$SiO—; $R^{22}$ and $R^{23}$ taken together are oxo.

Ascomycin (15 g) was dissolved in a solution of imidazole (3.75 g) in dry N,N-dimethylformamide (200 mL) and tert-butyldimethylchlorosilane (18.3 g) was added in portions and stirred at room temperature for 90 hours. N,N-dimethylformamide and excess tert-butyldimethylchlorosilane were removed by distillation (bath 30° C. at 0.8 torr.). The solid residue was extracted with anhydrous ether (4×50 mL). Ether was removed in vacuo and the solid residue was purified by silica gel chromatography eluting with 5% acetone in hexanes providing the title compound (17 g). MS (FAB) m/z: M+H=1022.

EXAMPLES 6a and 6b

Formula I: R=ethyl; R'=$R^2$=$R^4$=$R^5$=$R^9$=H; n=1; $R^3$=$OCH_3$; $R^1$=t-Bu$(CH_3)_2$SiO— (R Configuration); $R^6$ and $R^7$ taken together are oxo; $R^8$=OH; Y=subformula Ia, wherein $R^{18}$=$R^{19}$=$R^{21}$=H; $R^{20}$=OH; $R^{22}$ and $R^{23}$ taken together are oxo; and Formula I; R=ethyl; R'=$R^2$=$R^4$=$R^5$=$R^9$=H; n=1; $R^3$=$OCH_3$; $R^1$=t-Bu$(CH_3)_2$SiO— (R Configuration); $R^6$ and $R^7$ taken together are oxo; $R^8$=OH; Y=subformula Ia, wherein $R^{18}$=$R^{19}$=H; $R^{20}$ and $R^{21}$ taken together are oxo; $R^{22}$ and $R^{23}$ taken together are oxo.

EXAMPLE 6a

Ascomycin (1.582 g, 2 mmol) was dissolved in 30 mL of methylene chloride, and tert-butyldimethylsilyl chloride (362 mg, 2.4 mmol) and imidazole (272 mg, 4 mmol) were added. It was then stirred at room temperature for 4 days. Saturated aqueous ammonium chloride solution (20 mL) was added, and the product was extracted with ethyl acetate (25 mL×3). The ethyl acetate layers were combined, washed with brine, dried over anhydrous magnesium sulfate, filtered and evaporated to dryness to yield 2.11 g of title compound.

EXAMPLE 6b

To a −78° C. solution of oxalyl chloride (96 uL, 1.1 mmol) in 5 mL of methylene chloride was added a solution of dimethylsulfoxide (156 uL, 2.2 mmol) in 4 mL of methylene chloride and the mixture was stirred at −78° C. After 30 min a solution of example 6a (453 mg, 0.5 mmol) in 5 mL of methylene chloride was added. The reaction was carried out at −78° C. for 1.5 hours with stirring and then triethylamine (696.9 uL, 5 mmol) was added. After stirring at −78° C. for 5 min, the mixture was then allowed to stand at room temperature for 30 min. The reaction mixture was partitioned between 40 mL of ethylacetate and 10 mL of 10%-$KHSO_4$ solution. The separated organic layer was washed with 10%-$KHSO_4$(3×), brine, and dried over anhydrous magnesium sulfate. Evaporation of the solvent gave 438 mg of the crude title compound. This was purified by silica gel column chromatography, eluting with 2.5% ethyl acetate in chloroform. Yield: 225.8 mg. MS (FAB) m/z: M+K=942; IR(KBr) 3500, 3440, 2950, 2935, 2880, 2860, 2820, 1740, 1720, 1650, 1630, 1580, 1460, 1445, 1380, 1360, 1325, 1280, 1250, 1220, 1195, 1170, 1135, 1105, 1090, 1040, 1030, 1005 $cm^{-1}$.

EXAMPLE 7

Formula I: R=ethyl; R'=$R^2$=$R^4$=$R^5$=$R^9$=H; n=1; $R^3$=$OCH_3$; $R^1$=OH(R Configuration); $R^6$ and $R^7$ taken together are oxo; $R^8$=OH; Y=subformula Ia, wherein $R^{18}$=$R^{19}$=H; $R^{20}$ and $R^{21}$ taken together are oxo; $R^{22}$ and $R^{23}$ taken together are oxo.

To a solution of acetonitrile (5 mL) and 48% hydrofluoric acid (100 uL) was added Example 6b (530 mg, 0.586 mmol) in acetonitrile (7 mL) dropwise, and the mixture was stirred at room temperature for 35 min. Ethyl acetate (60 mL) was added to the reaction mixture, and the organic layer was washed with brine, 10%-$NaHCO_3$, brine, and dried over anhydrous magnesium sulfate. Evaporation of the solvent gave 515 mg of crude title compound which was purified by silica gel column chromatography, eluting with 1%-methanol in chloroform. 304.8 mg of pure compound was obtained. MS(FAB)m/z: M+K=828; IR(KBr) 3420, 2960, 2930, 2870, 2820, 1740, 1720, 1645, 1620, 1580, 1450, 1380, 1345, 1325, 1280, 1260, 1245, 1220, 1195, 1170, 1140, 1115, 1100, 1090, 1050, 1035, 1010 $cm^{-1}$.

EXAMPLE 8

Formula I: R=ethyl; R'=$R^2$=$R^4$=$R^5$=$R^9$=H; n=1; $R^3$=$OCH_3$; $R^1$=OH(R Configuration); $R^6$ and $R^7$ taken together are oxo; $R^8$=OH; Y=subformula Ib.

A solution of the product of Example 7 (0.5 g) and hydroxyethylhydrazine (0.0723 g) in absolute ethanol (10 mL) was reflected under nitrogen. Solvent was removed in vacuo, and product (0.229 g) was purified by silica gel chromatography eluting with 3% methanol in dichloromethane. MS (FAB) m/z: M+H=830.

EXAMPLE 9

Formula I: R=ethyl; R'=$R^2$=$R^4$=$R^5$=$R^9$=H; n=1; $R^3$=$OCH_3$; $R^1$=OC(NH)$CCl_3$ (R Configuration); $R^6$ and $R^7$ taken together are oxo; $R^8$=OH; Y=subformula Ia, wherein $R^{18}$=$R^{19}$=$R^{21}$=H; $R^{20}$=OH; $R^{22}$ and $R^{23}$ taken together are oxo.

EXAMPLE 9a

Formula I: R=ethyl; R'=$R^2$=$R^4$=$R^5$=$R^9$=H; n=1; $R^3$=$OCH_3$; $R^1$=OH (R Configuration); $R^6$ and $R^7$ taken together are oxo; $R^8$=OH; Y=subformula Ia, wherein $R^{18}$=$R^{19}$=$R^{21}$=H; $R^{20}$=t-Bu$(CH_3)_2$Si—O—; $R^{22}$ and $R^{23}$ taken together are oxo.

To a solution of 48% hydrogen fluoride aqueous solution (5 mL) was added Example 5 (32 g, 0.031 mol) in acetonitrile (500 mL), and the mixture was stirred at room temperature for 90 minutes. It was cooled to 0° C. in an ice bath, and solid $NaHCO_3$ was added to the reaction mixture. It was stirred for 1 hour and solid was removed by filtration. Acetonitrile was removed in vacuo and ethyl acetate (500 mL) was added to the residue, and the organic layer was washed with 10%-$NaHCO_3$ (300 mL×3), brine (250 mL), 10%-$NaHSO_4$ (300 mL×3), and brine (350 mL×3), and dried over anhydrous sodium sulfate. Evaporation of the solvent gave 35 g of crude title compound which was purified by silica gel column chromatography, followed by HPLC eluting with 25%-acetone in hexane. 24.28 g(85%) of pure compound was obtained. MS (FAB) m/z: M+K=844; In addition to the title compound, unreacted starting material (Example 5, 1.5 g) and ascomycin (500 mg) were isolated in pure form.

EXAMPLE 9b

Formula I: R=ethyl; R'=$R^2$=$R^4$=$R^5$=$R^9$=H; n=1; $R^3$=$OCH_3$; $R^1$=OC(NH)$CCl_3$ (R Configuration); $R^6$ and $R^7$ taken together are oxo; $R^8$=OH; Y=subformula Ia, wherein $R^{18}$=$R^{19}$=$R^{21}$=H; $R^{20}$=t-Bu$(CH_3)_2$Si—O—; $R^{22}$ and $R^{23}$ taken together are oxo.

The product of Example 9a (905 mg, 1 mmol) was dissolved in 20 mL of methylene chloride at room temperature. Glycerol formal trichloroimidate (1.243 g, 5 mmol) and boron trifluoride etherate (73.8 uL, 0.6 mmol) were added and stirred for one over night. Methylene chloride was removed by evaporation, and ethyl acetate (50 mL) was added to the residue. The ethyl acetate layer was washed with brine, 10% sodium bicarbonate (20 mL×3), brine, 10% potassium hydrogen sulfate (20 mL×3), brine and then dried over sodium sulfate. Solvent was removed to yield 2.24 g of crude product which was then purified by silica gel chromatography, eluting with 10% acetone in n-hexane. 800 mg of the title compound was isolated in 74% yield. MS(FAB) m/z: M+K=1090.

EXAMPLE 9

Formula I: R=ethyl; R'=$R^2$=$R^4$=$R^5$=$R^9$=H; n=1; $R^3$=$OCH_3$; $R^1$=OC(NH)$CCl_3$ (R Configuration); $R^6$ and $R^7$ taken together are oxo; $R^8$=OH; Y=subformula Ia, wherein $R^{18}$=$R^{19}$=$R^{21}$=H; $R^{20}$=OH; $R^{22}$ and $R^{23}$ taken together are oxo.

The product of Example 9b (800 mg, 0.73 mmol) was dissolved in 20 mL of acetonitrile at room temperature, 48% aqueous hydrogen fluoride solution (1 uL) was added and stirred for two hours. After being cooled in an ice bath, solid sodium hydrogen sulfate was added and stirred data 0° C. for an additional one hour. Solid was filtered and the filtrate was evaporated to dryness. The residue was re-dissolved in methylene chloride and passed through silica gel column, eluting with 15% acetone in n-hexane. The obtained crude product (680 mg) was finally purified by HPLC (column: microsorb, 1 inch diameter ×25 cm length; solvent: 20% acetone in n-hexane). The title compound (Example 208; 369.7 mg) was isolated in 57.4% yield. MS(FAB) m/z: M+K=976.

EXAMPLE 10

Formula I: R=ethyl; R'=$R^2$=$R^4$=$R^5$=$R^9$=H; n=1; $R^3$=$OCH_3$; $R^1$=$(C_6H_5O)_2$P(O)O (R Configuration); $R^6$ and $R^7$ taken together are oxo; $R^8$=OH; Y=subformula Ia, wherein $R^{18}$=$R^{19}$=$R^{21}$=H; $R^{20}$=$(C_6H_5O)_2$P(O)O—; $R^{22}$ and $R^{23}$ taken together are oxo.

Ascomycin (500 mg, 0.632 mmol) was dissolved in 6 mL of benzene in an ice bath, and triethylamine (264 uL, 1.9 mmol) followed by diphenylchlorophosphate (393 uL, 1.9 mmol) in benzene (5 mL) was added dropwise. After 4-dimethylaminopyridine (DMAP) (100 mg, 0.82 mmol) was added, it was then stirred at room temperature for 1 hour. 10%-Sodium bisulfate (5 uL) was added to the cooled reaction mixture. After additional benzene (20 mL) was added, the organic layer separated was with 10%-$NaHCO_3$ (40 mL×3), brine (×5) and then dried over anhydrous magnesium sulfate. Evaporation of the solvent gave 860 mg of crude product which was purified by flash silica gel (120 g), column chromatography, eluting with 25%-acetone in hexane. 656 mg of pure title compound was isolated. MS(FAB) m/z: M+K=1294.

EXAMPLE 11

Formula I: R=ethyl; R'=$R^2$=$R^4$=$R^5$=$R^9$=H; n=1; $R^3$=$OCH_3$; $R^1$=—OC(O)— (ortho-$NO_2$)-$C_6H_4$ (R configuration); $R^6$ and $R^7$ taken together are oxo; $R^8$=OH; Y=subformula Ia, wherein $R^{18}$=$R^{19}$; =$R^{21}$=H; $R^{20}$=OH; $R^{22}$ and $R^{23}$ taken together are oxo.

Ascomycin (791 mg, 1.0 mmol) and triethylamine (0.28 mL, 2.0 mmol) in dichloromethane (10 mL) were cooled to 0° C. 2-Nitrobenzoylchloride (322 uL, 2.2 mmol) was added followed by DMAP (122 mg, 1.0 mmol). Warmed the mixture to room temperature and after 24 hours the solution between 1N $H_3PO_4$ (30 mL) and EtOAc (30 mL). The aqueous layer was extracted again with EtOAc (30 mL). The organics were washed with brine (2×30 mL), combined, dried ($Na_2SO_4$) and concentrated in vacuo. The residue was purified by HPLC on silica gel eluting with hexane: acetone (2.5:1) providing the title compound in 40% yield. MS(FAB) m/z 979 (M+K).

EXAMPLE 12

Formula I: R=ethyl; R'=$R^2$=$R^4$=$R^5$=$R^9$=H; n=1; $R^3$=$OCH_3$; $R^1$=—OC(O)— (ortho-$NO_2$)—$C_6H_4$ (R configuration); $R^6$ and $R^7$ taken together are oxo; $R^8$=OH; Y=subformula Ia, wherein $R^{18}$=$R^{19}$=$R^{21}$=H; $R^{20}$=—OC(O)—(ortho-$NO_2$)—$C_6H_4$; $R^{22}$ and $R^{23}$ taken together are oxo.

Also isolated from the products of Example 11 was the title compound. MS(FAB) m/z 1128 (M+K).

EXAMPLE 13

Formula I: R=ethyl; R'=$R^2$=$R^4$=$R^5$=$R^9$=H; n=1; $R^3$=$OCH_3$; $R^1$=—OC(O)-2-pyridyl (R configuration); $R^6$ and $R^7$ taken together are oxo; $R^8$=OH; Y=subformula Ia, wherein $R^{18}$=$R^{19}$=$R^{21}$=H; $R^{20}$=OH; $R^{22}$ and $R^{23}$ taken together are oxo.

1-(3-Dimethylaminopropyl)-3-ethylcarbodiimide hydrochloride (700 mg, 3.7 mmol) was added at 0° C. to ascomycin (791 mg, 1.0 mmol), picolinic acid (381 mg, 3.1 mmol) and triethylamine (0.28 mL, 2.0 mmol) in dichloromethane (10 mL) followed by DMAP (122 mg, 1.0 mmol). The mixture was warmed to room temperature and stirred for 36 hours, whereupon it was partitioned between EtOAc (30 mL) and water (30 mL). Organics washed with brine (2×30 mL). Aqueous portions reextracted with EtOAc (30 mL), organics were combined, dried ($Na_2SO_4$) and concentrated in vacuo. Residue was purified by HPLC on silica gel eluting with hexane:acetone (1:1) to provide the title compound. MS(FAB) m/z 935 (M+K).

EXAMPLE 14

Formula I: R=ethyl; R'=$R^2$=$R^4$=$R^5$=$R^9$=H; n=1; $R^3$=$OCH_3$; $R^1$=—OC(O)-2-pyridyl (R configuration); $R^6$ and $R^7$ taken together are oxo; $R^8$=OH; Y=subformula Ia, wherein $R^{18}$=$R^{21}$=H; $R^{19}$ and $R^{20}$ taken together form a bond; $R^{22}$ and $R^{23}$ taken together are oxo.

Also isolated from the products of Example 13 was the title compound. MS(FAB) m/z 917 (M+K).

EXAMPLE 15

Formula I: R=ethyl; R'=$R^2$=$R^4$=$R^5$=$R^9$=H; n=1; $R^3$=$OCH_3$; $R^1$=—OC(O)-2-pyridyl (R configuration); $R^6$ and $R^7$ taken together are oxo; $R^8$=OH; Y=subformula Ia, wherein $R^{18}$=$R^{19}$=$R^{21}$=H; $R^{20}$=—OC(O)-2-pyridyl; $R^{22}$ and $R^{23}$ taken together are oxo. Also isolated from the products of Example 13 was the title compound. MS(FAB) m/z 1040 (M+K).

EXAMPLE 16

Formula I: R=ethyl; R'=$R^2$=$R^4$=$R^5$=$R^9$=H; n=1; $R^3$=$OCH_3$; $R^1$=OH (R configuration); $R^6$ and $R^7$ taken together are oxo; $R^8$=OH; Y=subformula Ia, wherein $R^{18}$=$R^{19}$=H; one of $R^{20}$ and $R^{21}$ is hydrogen and the other=N-benzylpiperazinyl; $R^{22}$ and $R^{23}$ taken together are oxo.

The product of Example 3 (500 mg, 0.65 mmol) was dissolved in 5 mL of methylene chloride containing 1-benzyl-piperazine (337 uL, 1.95 mmol) and triethylamine (270 uL, 1.95 mmol). The mixture was stirred at room temperature for one over night. Ethyl acetate (50 mL) and brine solution were added and partitioned. The ethyl acetate layer was washed with brine (×3), dried over anhydrous magnesium sulfate. Purification was carried out by silica gel column, followed by HPLC to obtain the title compound. Yield 159 mg (26%), MS(FAB) m/z: M+H =950, M+K=988.

EXAMPLE 17

Formula I: R=ethyl; R'=$R^2$=$R^4$=$R^5$=$R^9$=H; n=1; $R^3$=$OCH_3$; $R^1$=OH(R configuration); $R^6$ and $R^7$ taken together are oxo; $R^8$=OH; Y=subformula Ia, wherein $R^{18}$=$R^{19}$=H; one of $R^{20}$ and $R^{21}$ is hydrogen and the other=N-methylpiperazinyl; $R^{22}$ and $R^{23}$ taken together are oxo.

The title compound was prepared from the product of Example 3 (700 mg, 0.91 mmol) and 1-methylpiperazine (507 uL, 4.55 mmol), according to the procedure described in Example 16. Yield 208 mg (26%), MS(FAB) m/z: M+H= 874, M+K=912.

EXAMPLE 18

Formula I: R=ethyl; R'=$R^2$=$R^4$=$R^5$=$R^9$=H; n=1; $R^3$=$OCH_3$; $R^1$=OH(R configuration); $R^6$ and $R^7$ taken together are oxo; $R^8$=OH; Y=subformula Ia, wherein $R^{18}$=$R^{19}$=H; one of $R^{20}$ and $R^{21}$ is hydrogen and the other=N-phenylpiperazinyl; $R^{22}$ and $R^{23}$ taken together are oxo.

The title compound was prepared from the product of Example 3 (500 mg, 0.65 mmol) and 1-phenylpiperazine (493 uL, 3.25 mmol), according to the procedure described in Example 16. Yield 248 mg (41%), MS(FAB) m/z: M+H= 936, M+K=974.

EXAMPLE 19

Formula I: R=ethyl; R'=$R^4$=$R^5$=$R^9$=H; n=1; $R^3$=$OCH_3$; $R^1$ and $R^2$ taken together are =N—NH—C(=O)—$NH_2$; $R^6$ and $R^7$ taken together are oxo; $R^8$=OH;

Y=subformula Ia, wherein $R^{18}$=$R^{19}$=$R^{21}$=H; $R^{20}$=H; $R^{22}$ and $R^{23}$ taken together are oxo.

A solution of the title compound of Example 4 (0.6 g), semicarbazide (0.09 g) and triethylamine (0.13 mL) in absolute ethanol (4 mL) was stirred at room temperature for 1 hour. Ethanol was removed in vacuo and the crude purified by silica gel chromatography (30 g) eluting with 20% acetone in hexanes. Yield: 0.33 g. MS(FAB) m/e: M+K= 885.

EXAMPLES 20

Formula I: R=ethyl; R'=$R^2$=$R^4$=$R^5$=$R^9$=H; n=1; $R^3$=$OCH_3$; $R^1$=—O(t-bu$(CH_3)_2$Si—) (R configuration); $R^6$ and $R^7$ taken together are oxo; $R^8$=OH; Y=subformula Ia, wherein $R^{18}$=$R^{19}$=$R^{21}$=H; $R^{20}$=OC(O)$CH_2$I; $R^{22}$ and $R^{23}$ taken together are oxo.

To a stirred solution of the resultant compound of example 6a (2.0 g, 2.2 mmol) and iodoacetic anhydride (0.78 g, 2.2 mmol) in $CH_2Cl_2$ (10 mL) was added DMAP (0.05 g, 0.44 mmol). After the reaction was stirred at room temperature for 18 h more iodoacetic anhydride (0.1 g, 0.26 mmol) was added to the reaction, and stirring was continued for 24 h. The reaction mixture was diluted with ethyl acetate, and then washed sequentially with 10% aqueous $NaHSO_4$, sat'd $NaHCO_3$ and brine to give 2.2 g of crude material. After purification (HPLC, Rainin microsorb column, eluting with 10% acetone: 90% hexane), 1.59 g of the titled compound was collected along with 0.23 g of the unreacted starting material.

EXAMPLE 21

Formula I: R=ethyl; R'=$R^2$=$R^4$=$R^5$=$R^9$=H; n=1; $R^3$=$OCH_3$; $R^1$=—OH (R configuration); $R^6$ and $R^7$ taken together are oxo; $R^8$=OH; Y=subformula Ia, wherein $R^{18}$=$R^{19}$=$R^{21}$=H; $R^{20}$=OC(O)$CH_2$I; $R^{22}$ and $R^{23}$ taken together are oxo.

The resultant compound of example 20 (1.59 g, 1.48 mmol) was treated with 48% aqueous HF (0.3 mL) in $CH_3CN$ (50 mL) for 45 minutes to five 1.29 g of the semi-pure product from which 0.54 g was further purified by HPLC (Rainin microsorb column, eluting with 30% acetone: 70% hexane), and 0.41 g was collected as pure title compound. MS(FAB) m/z: M+K=998.

EXAMPLES 22

Formula I: R=ethyl; R'=$R^2$=$R^4$=$R^5$=$R^9$=H; n=1; $R^3$=$OCH_3$; $R^1$=—OC(O)$CH_2$I (R configuration); $R^6$ and $R^7$ taken together are oxo; $R^8$=OH; Y=subformula Ia, wherein $R^{18}$=$R^{19}$=$R^{21}$=H; $R^{20}$=—O—(t-Bu$(CH_3)_2$Si); $R^{22}$ and $R^{23}$ taken together are oxo.

Following the procedure of example 20, but replacing the resultant compound of example 6a with the resultant compound of 9a provided the desired product.

EXAMPLE 23

Formula I: R=ethyl; R'=$R^2$=$R^4$=$R^5$=$R^9$=H; n=1; $R^3$=$OCH_3$; $R^1$=—OC(O)$CH_2$I (R configuration); $R^6$ and $R^7$ taken together are oxo; $R^8$=OH; Y=subformula Ia, wherein $R^{18}$=$R^{19}$=$R^{21}$=H; $R^{20}$=—OH; $R^{22}$ and $R^{23}$ taken together are oxo.

Following the procedure of example 21, but replacing the resultant compound of example 20 with the resultant compound of example 22 provided the desired product. MS(FAB) m/z: M+K=998.

EXAMPLE 24

Formula I: R=ethyl; R'=$R^2$=$R^4$=$R^5$=$R^9$=H; n=1; $R^3$=$OCH_3$; $R^1$=—OC(O)$CH_2$I (R configuration); $R^6$ and $R^7$ taken together are oxo; $R^8$=OH; Y=subformula Ia, wherein $R^{18}$=$R^{19}$=$R^{21}$=H; $R^{20}$=—OC(O)$CH_2$I; $R^{22}$ and $R^{23}$ taken together are oxo.

To a stirred solution of ascomycin (0.500 g, 0.632 mmol) and iodoacetic anhydride (0.28 g, 0.79 mmol) in $CH_2Cl_2$ (0.63 mL) was added DMAP (7.7 mg, 0.063 mmol). After the reaction was stirred at room temperature for 50 h, more iodoacetic anhydride (0.112 g, 0.316 mmol) was added to the reaction, and stirring was continued for 48 h. The reaction mixture was evaporated and chromatographed to give the desired product. MS (FAB) m/z: M+K=1114.

EXAMPLE 25

Formula I: R=ethyl; R'=$R^2$=$R^4$=$R^9$=H; n=1; $R^3$=$OCH_3$; $R^1$=—OH (R configuration); $R^6$ and $R^7$ taken together are oxo; $R^5$=$R^8$=OH; Y=subformula Ia, wherein $R^{18}$=$R^{19}$=$R^{21}$=H; $R^{20}$=$OC(O)CH_2I$; $R^{22}$ and $R^{23}$ taken together are oxo.

To a stirred solution of selenium (IV) oxide (0.26 g, 2.3 mmol) in THF (8 mL) and water (1 mL) was added a 3M solution of tert-butyl hydroperoxide in 2,2,4-trimethylpentane (2.08 mL, 6.2 mmol). After stirring at room temperature for 10 minutes, the resultant product of example 21 (0.75 g, 0.78 mmol) was added to the reaction. The stirring was continued and the reaction was monitored by TLC. After the reaction was close to completion (7 days), it was partitioned between ethyl acetate and brine. The organic layer was separated and dried over $Na_2SO_4$. Filtration and evaporation of the solvent gave 0.67 g of the crude product which was purified by HPLC (microsorb column, eluting 35% acetone: 65% hexane) to give 0.24 g of the title compound in 32% yield. MS(FAB) m/z: M+K=1014.

EXAMPLE 26

Formula I: R=ethyl; R'=$R^2$=$R^4$=$R^9$=H; n=1; $R^3$=$OCH_3$; $R^1$=—$OC(O)CH_2I$ (R configuration); $R^6$ and $R^7$ taken together are oxo; $R^5$=$R^8$=OH; Y=subformula Ia, wherein $R^{18}$=$R^{19}$=$R^{21}$=H; $R^{20}$=—OH; $R^{22}$ and $R^{23}$ taken together are oxo.

Following the procedure of example 25, but replacing the resultant compound of example 21 with the resultant compound of example 23 provided the desired product. MS(FAB) m/z: M+K=1014.

EXAMPLE 27

Formula I: R=ethyl; R'=$R^2$=$R^4$=$R^5$=$R^9$=H; n=1; $R^3$=$OCH_3$; $R^1$=OH (R configuration); $R^6$ and $R^7$ taken together are oxo; $R^8$=OH; Y=subformula Ia, wherein $R^{18}$=$R^{19}$=H; one of $R^{20}$ and $R^{21}$ is hydrogen and the other= piperazinyl; $R^{22}$ and $R^{23}$ taken together are oxo.

The title compound was prepared from the product of Example 3 (700 mg, 0.91 mmol) and piperazine (498 mL, 4.55 mmol) according to the procedures described in Example 16. Yield 198 mg (24%), MS(FAB) m/z: M+K= 898

EXAMPLE 28

In Vivo Assay of Biological Activity

The immunosuppressant activity of the compounds of the present invention was determined using the human mixed lymphocyte reaction (MLR) assay described by Kino, T. et al. in *Transplantation Proceedings*, XIX(5):36–39, Suppl. 6(1987). The results of the assay, shown below in Table 1, demonstrate that the compounds tested are effective immunomodulators at sub-micromolar concentrations.

TABLE 1

| Ex. # | $IC_{50}$ (M) |
|---|---|
| 1 | $0.7 \times 10^{-9}$ |
| 3 | $80.0 \times 10^{-9}$ |
| 4 | $0.4 \times 10^{-9}$ |
| 7 | $113.3 \times 10^{-9}$ |
| 8 | $380.0 \times 10^{-9}$ |
| 9 | $0.2 \times 10^{-10}$ |
| 10 | $11.1 \times 10^{-9}$ |
| 16 | $190.8 \times 10^{-9}$ |
| 17 | $47.4 \times 10^{-9}$ |
| 18 | $119.0 \times 10^{-9}$ |
| 19 | $0.1 \times 10^{-10}$ |
| 21 | $9.3 \times 10^{-9}$ |
| 23 | $1.4 \times 10^{-9}$ |
| 24 | $178.0 \times 10^{-9}$ |
| 25 | $203.0 \times 10^{-9}$ |
| 26 | $125.0 \times 10^{-9}$ |
| 27 | $520.9 \times 10^{-9}$ |

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

What is claimed is:

1. A compound having the formula:

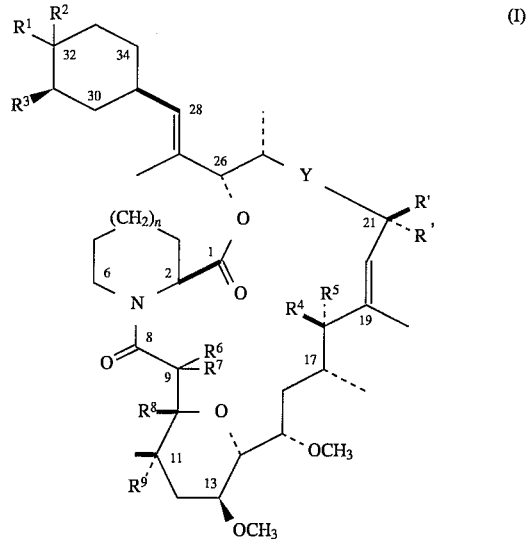

or a pharmaceutically acceptable salt, ester, amide or prodrug thereof wherein the ester is selected from $C_1$-to-$C_6$ alkyl esters, $C_5$-to-$C_7$ cycloalkyl esters and aryl-$C_1$-to-$C_{12}$-alkyl esters and wherein the amide results from reaction of a carboxylic acid moiety in the compound of formula I with $NH_3$, $NH_2(C_1$-to-$C_6$ alkyl), $NH(C_1$-to-$C_6$ alkyl)$_2$ or a 5- or 6-membered heterocycle containing one nitrogen atom and wherein the prodrug is selected from the group consisting of (a) acyloxymethyl esters of carboxylic acids, (b) (5-methyl-2-oxo-1,3-dioxolen-4-yl)methyl esters of carboxylic acids, (c) esters derived from alcohol groups in the parent drug by reaction with succinic acid, phosphoric acid, dialkylaminoacetic acid or an amino acid (d) N-Mannich bases of amides or amines, (e) N-hydroxymethyl derivatives of amides, (f) N-acyloxyalkyl derivatives of amides or heterocyclic amines, (g) oxazolidinones derived from ketone groups in the parent drug by reaction with 2-aminoethanol, N-methyl-2-aminoethanol, N-(2-hydroxyethyl)-2-aminoethanol, 2-aminopropanol, 2-amino-2-methylpropanol, 2-amino-2-hydroxymethylpropanol, 3-amino-2-hydroxypropane, 2-amino-1-phenylethanol, 3-aminopropanol or N-methyl-2-amino-1-phenylpropanol and (h) enol esters derived from ketone groups in the parent drug, wherein n is zero or one;

R and R' are chosen such that one of R and R' is hydrogen, and the other is selected from the group consisting of methyl, ethyl, 2-hydroxyethyl, propyl, cyclopropylmethyl, 2-oxopropyl, 2-ethanal and allyl;

$R^1$ is hydrogen, and $R^2$ and $R^3$ are independently selected from the group consisting of:
(a) $-OC(S)OR^{10}$, with the proviso that one of $R^{20}$ and $R^{21}$ is simultaneously $-OC(S)OR^{12}$ wherein $R^{10}$, $R^{20}$, $R^{21}$ and $R^{12}$ are as defined herein;
(b) $-OC(O)R^{14}$; with the proviso that one of $R^{20}$ and $R^{21}$ is simultaneously $-OC(O)R^{15}$ wherein $R^{14}$, $R^{20}$, $R^{21}$ and $R^{15}$ are as defined herein,
(c) $-C(=NH)CCl_3$;
(d) $-OC(O)CH_2I$;
(e) $-OP(O)(OR^{10})_2$ wherein $R^{10}$ is as defined herein; and
(f) $C_1$-to-$C_8$-loweralkoxy, with the proviso that $R^2$ and $R^3$ may not both be $C_1$-to-$C_8$-loweralkoxy;
or, taken together, $R^1$ and $R^2$ are $=NNHC(O)NH_2$;

$R^4$ and $R^5$ are selected from the group consisting of:
(a) hydrogen;
(b) $-OR^{11}$ wherein $R^{11}$ is as defined herein;
(c) halogen; and
(d) hydroxy, with the proviso that when one of $R^4$ and $R^5$ is hydroxy, the other of $R^4$ and $R^5$ is hydrogen;
or, taken together, $R^4$ and $R^5$ form a divalent radical selected from the group consisting of oxo and thiooxo;

Y is a group selected from the subformulae:

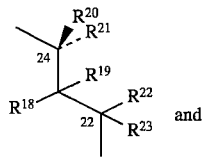 (Ia)

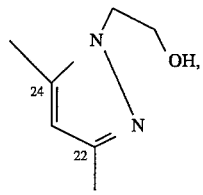 (Ib)

wherein $R^{18}$ and $R^{19}$ are chosen such that:
(i) both of $R^{18}$ and $R^{19}$ are hydrogen, or
(ii) one of $R^{18}$ and $R^{19}$, taken together with one of $R^{20}$ and $R^{21}$, forms a C-23/C-24 bond, and the other of $R^{18}$ and $R^{19}$ is hydrogen;

$R^{20}$ and $R^{21}$ are chosen such that:
(i) one of $R^{20}$ and $R^{21}$ is hydrogen, and the other of $R^{20}$ and $R^{21}$ is selected from the group consisting of:
(a) hydrogen,
(b) hydroxy,
(c) amino,
(d) $-N(CH_2CH_2)_2N-R^{12}$ wherein $R^{12}$ is as defined herein,
(e) $-N(CH_2CH_2)_2NH$,
(f) $-OR^{12}$ wherein $R^{12}$ is as defined herein,
(g) $-OC(O)NHR^{24}$, wherein $R^{24}$ is selected from the group consisting of:
(1) hydrogen,
(2) $C_1$-to-$C_8$-loweralkyl, and
(3) aryl,
(h) $-C(O)R^{12}$ wherein $R^{12}$ is as defined herein,
(i) $-OC(S)OR^{12}$ wherein $R^{12}$ is as defined herein,
(j) $-OC(O)R^{15}$ wherein $R^{15}$ is as defined herein,
(k) $-OC(O)CH_2I$, and
(l) $-O-$[(hydroxy protecting group)]protected by a hydroxy-protecting group selected from methylthiomethyl tert-butyldimethylsilyl, tert-butyldiphenylsilyl, aryl-C(O)— and $C_1$-to-$C_{12}$-alkyl-C(O)— and; or
(ii) one of $R^{20}$ and $R^{21}$, taken together with one of $R^{18}$ and $R^{19}$, forms a C-23/C-24 bond, and the other of $R^{20}$ and $R^{21}$ is selected from the group consisting of:
(a) hydrogen,
(b) hydroxy, and
(c) $C_1$-to-$C_8$-loweralkoxy;
or, taken together, $R^{20}$ and $R^{21}$ form an oxo group;

$R^{22}$ and $R^{23}$ are chosen such that:
(i) both are $C_1$-to-$C_8$-loweralkoxy; or
(ii) one of $R^{22}$ and $R^{23}$ is hydrogen, and the other is selected from the group consisting of:
(a) hydroxy,
(b) $-OC(O)R^{13}$ wherein $r^{13}$ is as defined herein, and
(c) $-OC(O)O$-(aryl-$C_1$-to-$C_{12}$-alkyl—);
or, taken together, $R^{22}$ and $R^{23}$ form an oxo group;

$R^6$ and $R^7$ are chosen such that:
(i) both of $R^6$ and $R^7$ are hydrogen;
(ii) one of $R^6$ and $R^7$ is hydrogen, and the other of $R^6$ and $R^7$, taken together with $R^8$, forms a C-9/C-10 bond;
(iii) one of $R^6$ and $R^7$ is hydroxy, and the other of $R^6$ and $R^7$ is selected from the group consisting of:
(a) hydrogen,
(b) $C_1$-to-$C_8$-loweralkyl,
(c) aryl-$C_1$-to-$C_{12}$-alkyl, and
(d) aryl;
or, taken together, $R^6$ and $R^7$ form a divalent radical selected from the group consisting of:
(a) oxo,
(b) $=NOH$,
(c) $=NNHC(O)NH_2$,
(d) $=NNR^{25}R^{26}$, where $R^{25}$ and $R^{26}$ are independently selected from the group consisting of:
(1) hydrogen,
(2) $C_1$-to-$C_8$-loweralkyl, and
(3) aryl,
(e) $=CH_2$,
(f) $-O-CH_2-$, and
(g) thiooxo;
or, taken together with the carbon to which they are attached, $R^6$ and $R^7$ are absent such that C-8 is attached directly to C-10;

$R^8$ is selected from the group consisting of:
(a) hydroxy,
(b) halogen,
(c) amino,
(d) $C_1$-to-$C_8$-loweralkylamino,
(e) aryl-$C_1$-to-$C_{12}$-alkylamino,
(f) $C_1$-to-$C_8$-loweralkoxy, and
(g) arylalkoxy;
or, taken together with one of $R^6$ and $R^7$ as defined above, forms a C-9/C-10 double bond;

or, taken together with $R^9$ as defined herein forms a C-10/C-11 double bond;

$R^9$ is hydrogen or, taken together with $R^8$ as defined above, forms a C-10/C-11 bond;

$R^{10}$, $R^{11}$, $R^{12}$ and $R^{13}$ are each independently selected from the group consisting of $C_1$-to-$C_8$-loweralkyl, aryl-$C_1$-to-$C_{12}$-alkyl and aryl; and $R^{14}$ and $R^{15}$ are each independently selected from the group consisting of:
(i) 2-nitro-aryl,
(ii) 3-nitro-aryl,
(iii) 4-nitro-aryl,
(iv) 2-pyridyl,
(v) 3-pyridyl, and
(vi) 4-pyridyl wherein at each occurrence the aryl group is selected from phenyl, 1-naphthyl, 2-naphthyl, fluorenyl, (1,2,)-dihydronaphthyl, (1,2,3,4)-tetrahydronaphthyl, indenyl and indanyl substituted by $R^{111}$, $R^{112}$ and $R^{113}$ wherein $R^{111}$, $R^{112}$ and $R^{113}$ are independently selected from the group consisting of:
(a) hydrogen,
(b) —$C_1$-to-$C_7$-alkyl,
(c) —$C_2$-to-$C_6$-alkenyl,
(d) halogen,
(e) —$(CH_2)_mN(C_1$-to-$C_3$-alkyl$)_2$, where m is zero to six,
(f) —CN,
(g) —CHO,
(h) mono-, di-, tri, or perhalogenated $C_1$-to-$C_{12}$-alkyl,
(i) —$S(O)_s(C_1$-to-$C_3$-alkyl), where s is zero, one or two,
(j) —$C(O)N(C_1$-to-$C_3$-alkyl$)_2$,
(k) —$(CH_2)_mO(C_1$-to-$C_3$-alkyl), where m is as defined above,
(l) —$CH(OR^{115})(OR^{116})$, where $R^{115}$ and $R^{116}$ are independently —$C_1$-to-$C_3$-alkyl or, taken together, form an ethylene or propylene bridge,
(m) —$(CH_2)_mOC(O)(C_1$-to-$C_3$-alkyl) where m is as defined above,
(n) —$(CH_2)_mC(O)O(C_1$-to-$C_3$-alkyl) where m is as defined above,
(o) —$OR^{117}$, where $R^{117}$ is selected from:
  (i) —PO(OH)OH,
  (ii) —$SO_3H$,
  (iii) —$C(O)(CH_2)_mC(O)OH$ where m is as defined above,
(p) —$S(O)_tN(C_1$-to-$C_3$-alkyl$)_2$ where t is one or two,
(q) —$NO_2$,
(r) —$N_3$,
(s) guanidino of the structure —$NR^{105}C(=NR^{106})NR^{107}$2 wherein $R^{105}$, $R^{106}$ and $R^{107}$ are independently selected from
  (i) hydrogen,
  (ii) $C_1$-to-$C_{12}$-alkyl,
  (iii) aryl-C(O)— or $C_1$-to-$C_{12}$-alkyl-C(O),
  (iv) aryl,
  (v) aryl-$SO_2$—,
  (vi) alkoxycarbonyl
  (vii) arylalkoxycarbonyl,
  (viii) arloxycarbonyl,
  (iv) $C_1$-to-$C_{12}$-alkyl-$SO_2$—
or taken together, $R^{106}$ and $R^{107}$ are —$(CH_2)_{cc}$— wherein cc is an integer of from 2 to 6 and
at each occurrence the heterocycle or heterocyclic group is independently selected from the group consisting of pyrrolyl, pyrrolidinyl, pyrazolyl, pyrazolinyl, pyrazolidinyl, cytosinyl, thiocytosinyl, imidazolyl, imidazolinyl, imidazolidinyl, pyridyl, piperidinyl, pyrazinyl, piperazinyl, pyrimidinyl, pyridazinyl, xanthenyl, xanthonyl, xanthopterinyl, oxazoyl, oxazolidinyl, thiouracilyl, isoxazolyl, isoxazolidinyl, morpholinyl, indolyl, quinolinyl, uracilyl, urazolyl, uricyl, thiazolyl, thiazolidinyl, isothiazolyl, isothiazolidinyl, isoquinolinyl, thymidinyl, benzimidazolyl, benzothiazolyl, benzoxazolyl, furyl, thienyl and benzothienyl wherein any carbon or heteroatom with suitable valence may bear a substituent selected at each occurrence from $R^{111}$, $R^{112}$ and $R^{113}$ independently as defined above.

2. A compound according to claim 1 wherein R and R' are selected from the group consisting of methyl, ethyl, propyl and allyl.

3. A compound according to claim 1 wherein $R^4$ and $R^5$ are both hydrogen.

4. A compound according to claim 1 wherein one of $R^4$ and $R^5$ is hydroxy, and the other of $R^4$ and $R^5$ is hydrogen.

5. A compound according to claim 1 wherein $R^{20}$ is hydroxy.

6. A compound according to claim 1 wherein $R^{20}$ and $R^{21}$ are both hydrogen.

7. A compound according to claim 1 wherein $R^{22}$ and $R^{23}$, taken together, form an oxo group.

8. A compound according to claim 1 wherein $R^6$ and $R^7$, taken together, form an oxo group.

9. A compound according to claim 1 wherein $R^8$ is hydroxy.

10. A compound according to claim 1 wherein $R^9$ is hydrogen.

11. A compound according to claim 1, selected from the group consisting of:
a compound of formula I in which R=ethyl; R'=$R^2$=$R^4$=$R^5$=$R^9$=H; n=1; $R^3$=$OCH_3$; $R^1$=$C_6H_5OC(S)O$ (R Configuration); $R^6$ and $R^7$ taken together are oxo; $R^8$=OH; Y=subformula Ia, wherein $R^{18}$=$R^{19}$=$R^{21}$=H; $R^{20}$=$C_6H_5OC(S)O$; $R^{22}$ and $R^{23}$ taken together are oxo;

a compound of Formula I in which R=ethyl; R'=$R^2$=$R^4$=$R^5$=$R^9$=H; n=1; $R^3$=$OCH_3$; $R^1$=OH (R Configuration); $R^6$ and $R^7$ taken together are oxo; $R^8$=OH; Y=subformula Ib;

a compound of Formula I in which R=ethyl; R'=$R^2$=$R^4$=$R^5$=$R^9$=H; n=1; $R^3$=$OCH_3$; $R^1$=OC(NH)$CCl_3$(R Configuration); $R^6$ and $R^7$ taken together are oxo; $R^8$=OH; Y=subformula Ia, wherein $R^{18}$=$R^{19}$=$R^{21}$=H; $R^{20}$=OH; $R^{22}$ and $R^{23}$ taken together are oxo;

a compound of Formula I in which R=ethyl; R'=$R^2$=$R^4$=$R^5$=$R^9$=H; n=1; $R^3$=$OCH_3$; $R^1$=OC(NH)$CCl_3$ (R Configuration); $R^6$ and $R^7$ taken together are oxo; $R^8$=OH; Y=subformula Ia, wherein $R^{18}$=$R^{19}$=$R^{21}$=H; $R^{20}$=t-Bu$(CH_3)_2$Si—O—; $R^{22}$ and $R^{23}$ taken together are oxo;

a compound of Formula I in which R=ethyl; R'=$R^2$=$R^4$=$R^5$=$R^9$=H; n=1; $R^3$=$OCH_3$; $R^1$=$(C_6H_5O)_2P(O)O$ (R Configuration); $R^6$ and $R^7$ taken together are oxo; $R^8$=OH; Y=subformula Ia, wherein $R^{18}$=$R^{19}$=$R^{21}$H; $R^{20}$=$(C_6H_5O)_2P(O)O$—; $R^{22}$ and $R^{23}$ taken together are oxo;

a compound of Formula I in which R=ethyl; R'=$R^2$=$R^4$=$R^5$=$R^9$=H; n=1; $R^3$=$OCH_3$; $R^1$=—OC(O)—(ortho-$NO_2$)-$C_6H_4$ (R configuration); $R^6$ and $R^7$ taken together are oxo; $R^8$=OH; Y=subformula Ia, wherein $R^{18}$=$R^{19}$=$R^{21}$=H; $R^{20}$=—OC(O)—(ortho-$NO_2$—$C_6H_4$; $R^{22}$ and $R^{23}$ taken together are oxo;

a compound of Formula I in which R=ethyl; R'=$R^2$=$R^4$=$R^5$=$R^9$=H; n=1; $R^3$=$OCH_3$; $R^1$=—OC(O)-2-pyridyl (R configuration); $R^6$ and $R^7$ taken together are oxo; $R^8$=OH; Y=subformula Ia, wherein $R^{18}$=$R^{19}$=$R^{21}$=H; $R^{20}$=—OC(O)—2-pyridyl; $R^{22}$ and $R^{23}$ taken together are oxo;

a compound of Formula I in which R=ethyl; R'=$R^2$=$R^4$=$R^5$=$R^9$=H; n=1; $R^3$=OCH$_3$; $R^1$=OH (R configuration); $R^6$ and $R^7$ taken together are oxo; $R^8$=OH; Y=subformula Ia, wherein $R^{18}$=$R^{19}$=H; one of $R^{20}$ and $R^{21}$ is hydrogen and the other =N-benzylpiperazinyl; $R^{22}$ and $R^{23}$ taken together are oxo;

a compound of Formula I in which R=ethyl; R'=$R^2$=$R^4$=$R^5$=$R^9$=H; n=1; $R^3$=OCH$_3$; $R^1$=OH (R configuration); $R^6$ and $R^7$ taken together are oxo; $R^8$=OH; Y=subformula Ia, wherein $R^{18}$=$R^{19}$=H; one of $R^{20}$ and $R^{21}$ is hydrogen and the other=N-methylpiperazinyl; $R^{22}$ and $R^{23}$ taken together are oxo;

a compound of Formula I in which R=ethyl; R'=$R^2$=$R^4$=$R^5$=$R^9$=H; n=1; $R^3$=OCH$_3$; $R^1$=OH (R configuration); $R^6$ and $R^7$ taken together are oxo; $R^8$=OH; Y=subformula Ia, wherein $R^{18}$=$R^{19}$=H; one of $R^{20}$ and $R^{21}$ is hydrogen and the other =N-phenylpiperazinyl; $R^{22}$ and $R^{23}$ taken together are oxo;

a compound of Formula I in which R=ethyl; R'=$R^4$=$R^5$=$R^9$=H; n=1; $R^3$=OCH$_3$; $R^1$ and $R^2$ taken together are =N—NH—C(=O)—NH$_2$; $R^6$ and $R^7$ taken together are oxo; $R^8$=OH; Y=subformula Ia, wherein $R^{18}$=$R^{19}$=$R^{21}$=H; $R^{20}$=H; $R^{22}$ and $R^{23}$ taken together are oxo;

a compound of Formula I in which R=ethyl; R'=$R^2$=$R^4$=$R^5$=$R^9$=H; n=1; $R^3$=OCH$_3$; $R^1$=—O(t-Bu(CH$_3$)$_2$Si—) (R configuration); $R^6$ and $R^7$ taken together are oxo; $R^8$=OH; Y=subformula Ia, wherein $R^{18}$=$R^{19}$=$R^{21}$=H; $R^{20}$=OC(O)CH$_2$I; $R^{22}$ and $R^{23}$ taken together are oxo;

a compound of Formula I in which R=ethyl; R'=$R^2$=$R^4$=$R^5$=$R^9$=H; n=1; $R^3$=OCH$_3$; $R^1$=—OH (R configuration); $R^6$ and $R^7$ taken together are oxo; $R^8$=OH; Y=subformula Ia, wherein $R^{18}$=$R^{19}$=$R^{21}$=H; $R^{20}$=OC(O)CH$_2$I; $R^{22}$ and $R^{23}$ taken together are oxo;

a compound of Formula I in which R=ethyl; R'=$R^2$=$R^4$=$R^5$=$R^9$=H; n=1; $R^3$=OCH$_3$; $R^1$=—OC(O)CH$_2$I (R configuration); $R^6$ and $R^7$ taken together are oxo; $R^8$=OH; Y=subformula Ia, wherein $R^{18}$=$R^{19}$=$R^{21}$=H; $R^{20}$=—O—(t-Bu(CH$_3$)$_2$Si); $R^{22}$ and $R^{23}$ taken together are oxo;

a compound of Formula I in which R=ethyl; R'=$R^2$=$R^4$=$R^5$=$R^9$=H; n=1; $R^3$=OCH$_3$; $R^1$=—OC(O)CH$_2$I (R configuration); $R^6$ and $R^7$ taken together are oxo; $R^8$=OH; Y=subformula Ia, wherein $R^{18}$=$R^{19}$=$R^{21}$=H; $R^{20}$=—OH; $R^{22}$ and $R^{23}$ taken together are oxo;

a compound of Formula I in which R=ethyl; R'=$R^2$=$R^4$=$R^5$=$R^9$=H; n=1; $R^3$=OCH$_3$; $R^1$=—OC(O)CH$_2$I (R configuration); $R^6$ and $R^7$ taken together are oxo; $R^8$=OH; Y=subformula Ia, wherein $R^{18}$=$R^{19}$=$R^{21}$=H; $R^{20}$=—OC(O)CH$_2$I; $R^{22}$ and $R^{23}$ taken together are oxo;

a compound of Formula I in which R=ethyl; R'=$R^2$=$R^4$=$R^9$=H; n=1; $R^3$=OCH$_3$; $R^1$=—OH (R configuration); $R^6$ and $R^7$ taken together are oxo; $R^5$=$R^8$=OH; Y=subformula Ia, wherein $R^{18}$=$R^{19}$=$R^{21}$=H; $R^{20}$=OC(O)CH$_2$I; $R^{22}$ and $R^{23}$ taken together are oxo;

a compound of Formula I in which R=ethyl; R'=$R^2$=$R^4$=$R^9$=H; n=1; $R^3$=OCH$_3$; $R^1$=—OC(O)CH$_2$I (R configuration); $R^6$ and $R^7$ taken together are oxo; $R^5$=$R^8$=OH; Y=subformula Ia, wherein $R^{18}$=$R^{19}$=$R^{21}$=H; $R^{20}$=—OH; $R^{22}$ and $R^{23}$ taken together are oxo; and a compound of Formula I in which R=ethyl; R'=$R^2$=$R^4$=$R^5$=$R^9$=H; n=1; $R^3$=OCH$_3$; $R^1$=OH (R configuration); $R^6$ and $R^7$ taken together are oxo; $R^8$=OH; Y=subformula Ia, wherein $R^{18}$=$R^{19}$=H; one of $R^{20}$ and $R^{21}$ is hydrogen and the other=piperazinyl; $R^{22}$ and $R^{23}$ taken together are oxo.

* * * * *

UNITED STATES PATENT AND TRADEMARK OFFICE
CERTIFICATE OF CORRECTION

PATENT NO. : 5,604,294
DATED : February 18, 1997
INVENTOR(S) : Luly et al.

It is certified that error appears in the above-indentified patent and that said Letters Patent is hereby corrected as shown below:

Column 34, line 12, delete "[(hydroxy protecting group)]".

Column 34, line 28, change "r$^{13}$" to --R$^{13}$--.

Column 35, line 53, change "NR$^{107}$2" to --NR$^{107}_2$--.

Signed and Sealed this

Seventh Day of October, 1997

Attest:

BRUCE LEHMAN

Attesting Officer     Commissioner of Patents and Trademarks